(12) United States Patent
Bianchi et al.

(10) Patent No.: US 12,279,941 B2
(45) Date of Patent: Apr. 22, 2025

(54) ABSORBENT ARTICLE WITH A DISTRIBUTION LAYER COMPRISING CHANNELS

(71) Applicant: The Procter & Gamble Company, Cincinnati, OH (US)

(72) Inventors: Ernesto Gabriel Bianchi, Oberursel (DE); Jörg Endres, Frankfurt am Main (DE); Alexander Fedotov, Schwalbach (DE); Julien René Garcia, Frankfurt (DE); Ryo Minoguchi, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 23 days.

(21) Appl. No.: 18/075,582

(22) Filed: Dec. 6, 2022

(65) Prior Publication Data

US 2023/0099991 A1    Mar. 30, 2023

Related U.S. Application Data

(62) Division of application No. 15/477,408, filed on Apr. 3, 2017, now abandoned.

(30) Foreign Application Priority Data

Apr. 29, 2016    (EP) .................................. 16167640

(51) Int. Cl.
    *A61F 13/537*    (2006.01)
    *A61F 13/15*    (2006.01)
    (Continued)

(52) U.S. Cl.
CPC .. *A61F 13/53747* (2013.01); *A61F 13/15203* (2013.01); *A61F 13/49* (2013.01);
(Continued)

(58) Field of Classification Search
CPC .......... A61F 13/53747; A61F 13/15203; A61F 13/49; A61F 13/532; A61F 13/535;
(Continued)

(56) References Cited

U.S. PATENT DOCUMENTS

| | | |
|---|---|---|
| 6,245,961 B1 | 6/2001 | Roxendal et al. |
| 8,267,910 B2 | 9/2012 | Perneborn |

(Continued)

FOREIGN PATENT DOCUMENTS

| | | |
|---|---|---|
| WO | 02085271 A1 | 10/2002 |
| WO | 2012048878 A1 | 4/2012 |

(Continued)

OTHER PUBLICATIONS

All Office Actions, U.S. Appl. No. 15/477,408.
(Continued)

*Primary Examiner* — Jessica Arble
(74) *Attorney, Agent, or Firm* — Anna E. Haller; Sarah M. DeCristofaro; Amanda Marie Herman Berghauer

(57) ABSTRACT

An absorbent article such as a diaper extending in a longitudinal direction parallel to a longitudinal axis (80') and a transversal direction (90') perpendicular to the longitudinal direction and comprising a distribution layer (54) between a topsheet (24) and an absorbent core (28). The distribution layer comprises a fibrous material and a first and second longitudinally-extending channels (86a,b) substantially free of fibrous material. The fibrous material is profiled in the transversal direction so that average basis weight between the channels differs from the average basis weight in the lateral areas outward of the channels by at least 50 g/m² and/or wherein the distribution layer comprises a first region having a first basis weight (bw1) and a second region having a second basis weight (bw2), wherein the first basis weight and the second basis weight differ by at least 20 g/m²,
(Continued)

preferably by at least 50 g/m², and these regions are present in different areas of the distribution layer but in the same longitudinally extending transversal section. The absorbent core may comprise channel-forming areas (26a,b). The article further comprises a backsheet (25).

12 Claims, 13 Drawing Sheets

(51) Int. Cl.
| | |
|---|---|
| A61F 13/49 | (2006.01) |
| A61F 13/53 | (2006.01) |
| A61F 13/532 | (2006.01) |
| A61F 13/534 | (2006.01) |
| A61F 13/535 | (2006.01) |
| A61F 13/551 | (2006.01) |
| A61L 15/28 | (2006.01) |
| B65D 85/07 | (2017.01) |
| B65D 85/62 | (2006.01) |

(52) U.S. Cl.
CPC .......... *A61F 13/532* (2013.01); *A61F 13/535* (2013.01); *A61F 13/537* (2013.01); *A61F 13/53717* (2013.01); *A61F 13/551* (2013.01); *A61F 13/55105* (2013.01); *A61L 15/28* (2013.01); *B65D 85/07* (2018.01); *B65D 85/62* (2013.01); *A61F 2013/15406* (2013.01); *A61F 2013/530138* (2013.01); *A61F 2013/530481* (2013.01); *A61F 2013/5349* (2013.01); *A61F 2013/53778* (2013.01)

(58) Field of Classification Search
CPC .............. A61F 13/537; A61F 13/53717; A61F 2013/15406
See application file for complete search history.

(56) References Cited

U.S. PATENT DOCUMENTS

| | | |
|---|---|---|
| 9,375,358 B2 | 6/2016 | Ehrnsperger et al. |
| 2002/0062113 A1 | 5/2002 | Thomas et al. |
| 2005/0148972 A1 | 7/2005 | Miyama et al. |
| 2008/0021426 A1 | 1/2008 | Nakagawa et al. |
| 2010/0292663 A1 | 11/2010 | Lavon et al. |
| 2012/0238983 A1 | 9/2012 | Vega |
| 2012/0316526 A1 | 12/2012 | Rosati et al. |
| 2014/0163504 A1* | 6/2014 | Bianchi ............ A61F 13/53717 604/374 |
| 2014/0303583 A1 | 10/2014 | Berrizbeitia et al. |
| 2015/0065981 A1* | 3/2015 | Roe .................... A61F 13/4756 604/378 |
| 2017/0312149 A1 | 11/2017 | Bianchi et al. |

FOREIGN PATENT DOCUMENTS

| | | |
|---|---|---|
| WO | 2014093310 A1 | 6/2014 |
| WO | 2014093323 A1 | 6/2014 |

OTHER PUBLICATIONS

Extended European Search Report and Search Opinion; Application Ser. No. 16167640.8; dated Sep. 30, 2016; 7 pages.
International Search Report and Written Opinion; Application Ser. No. PCT/US2017/025826; dated Jun. 23, 2017; 12 pages.

\* cited by examiner

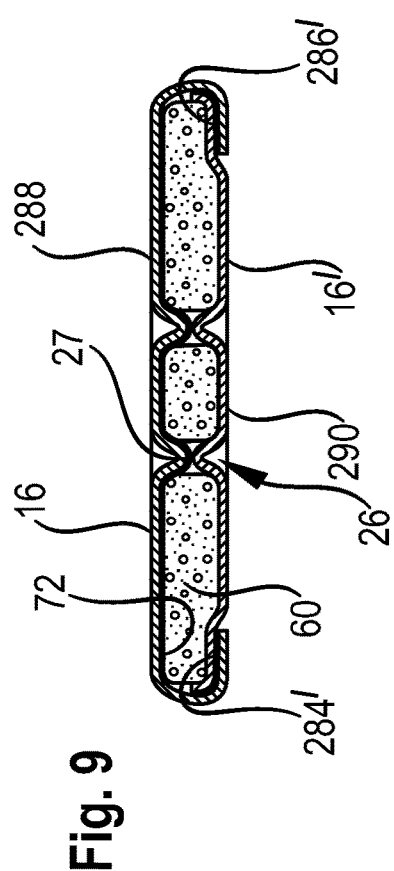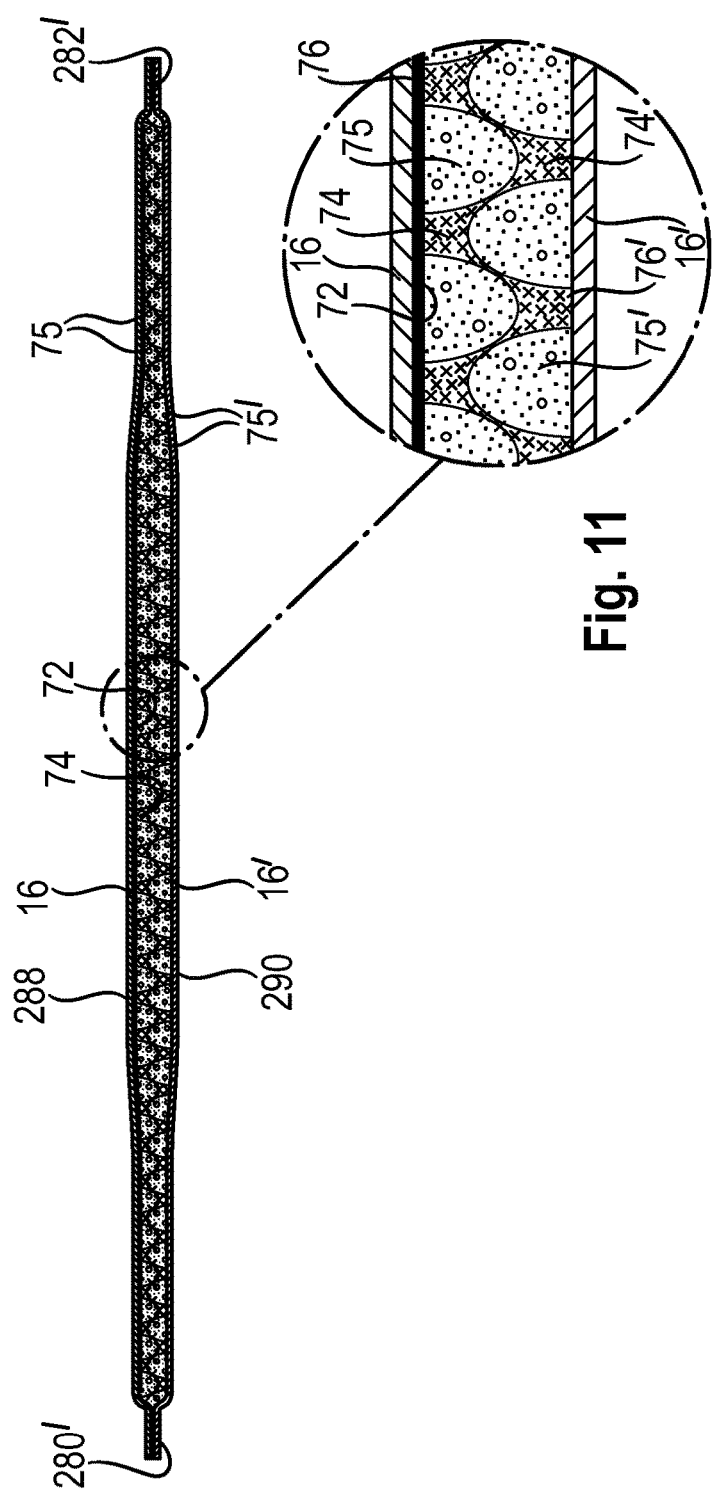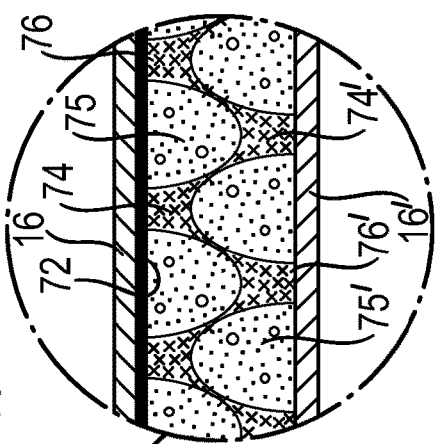

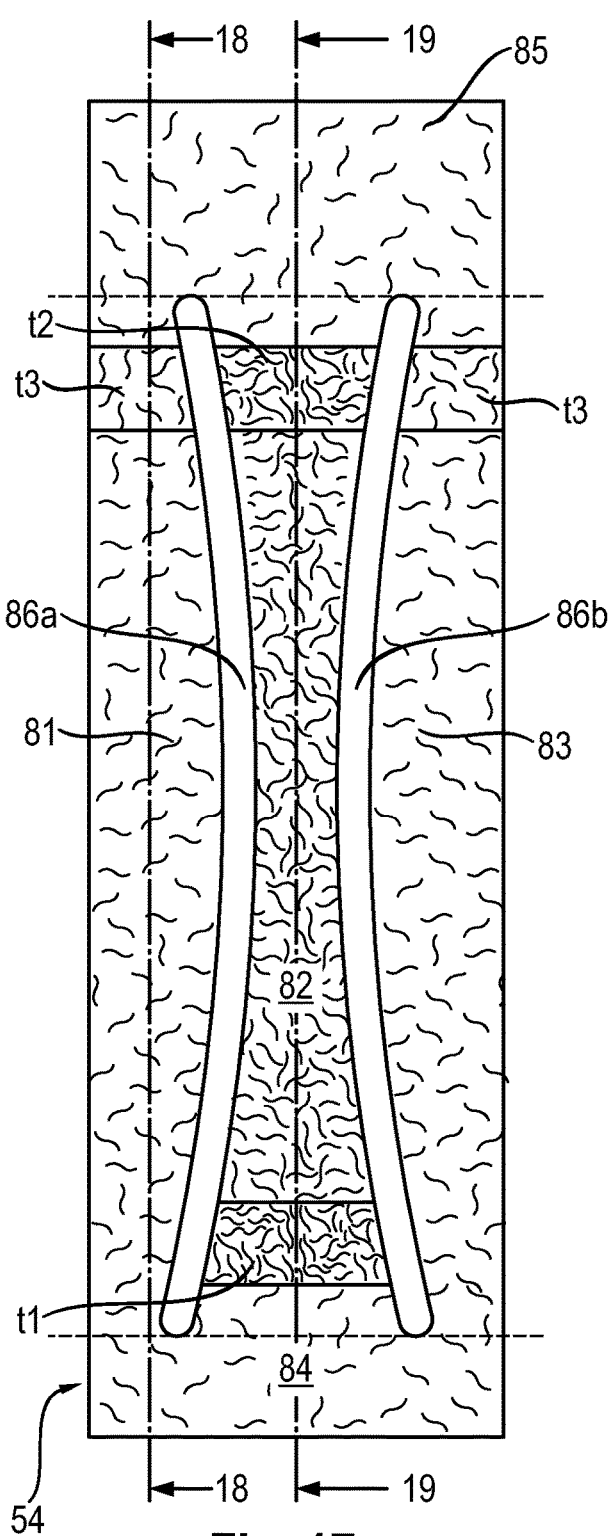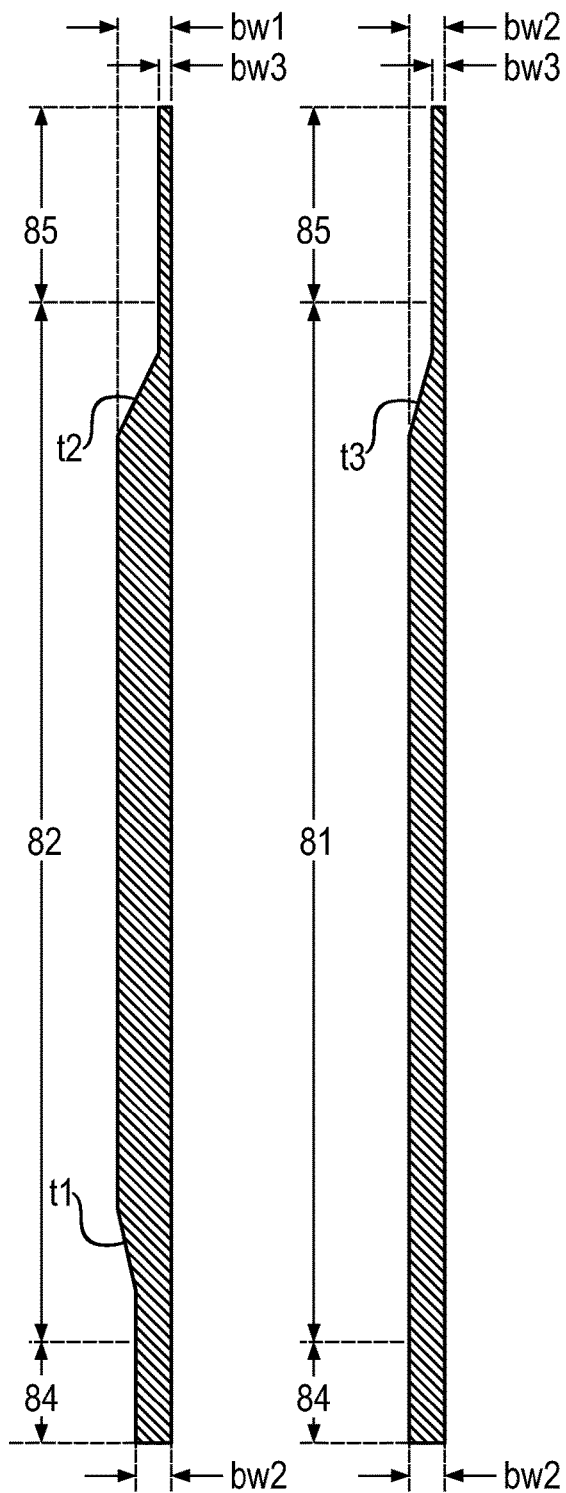
Fig. 17   Fig. 18   Fig. 19

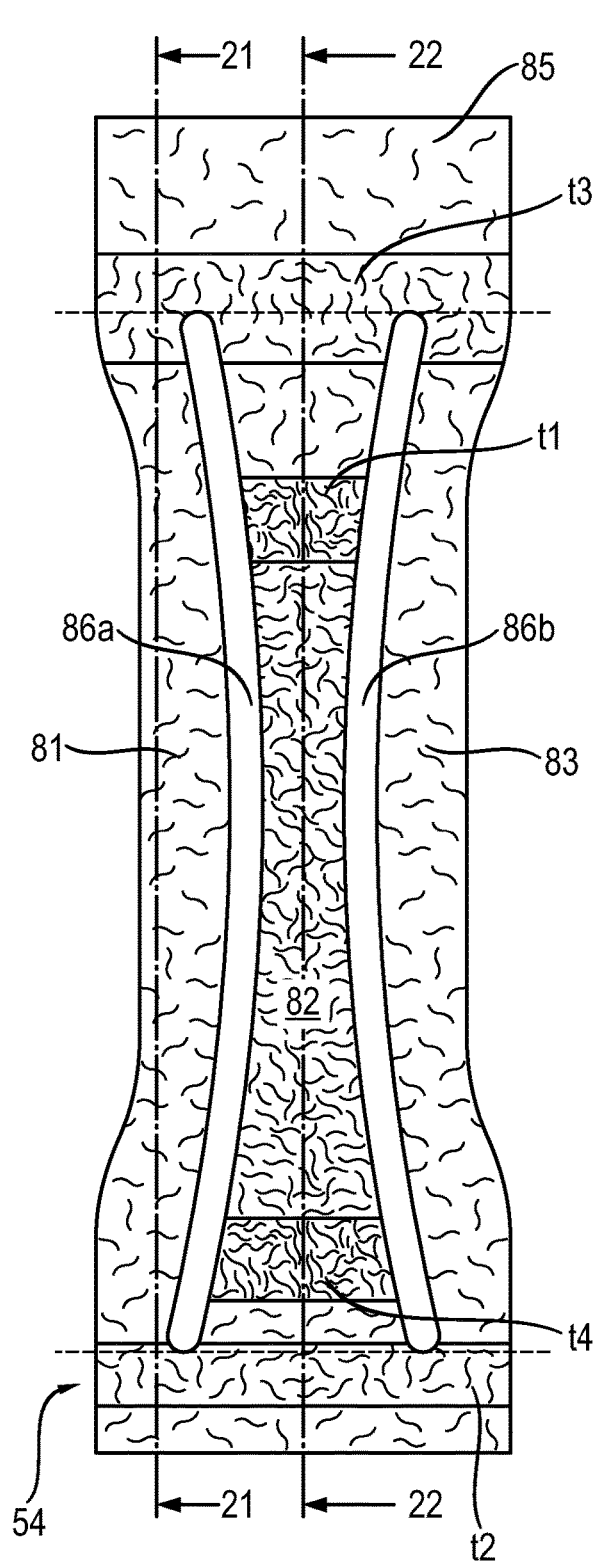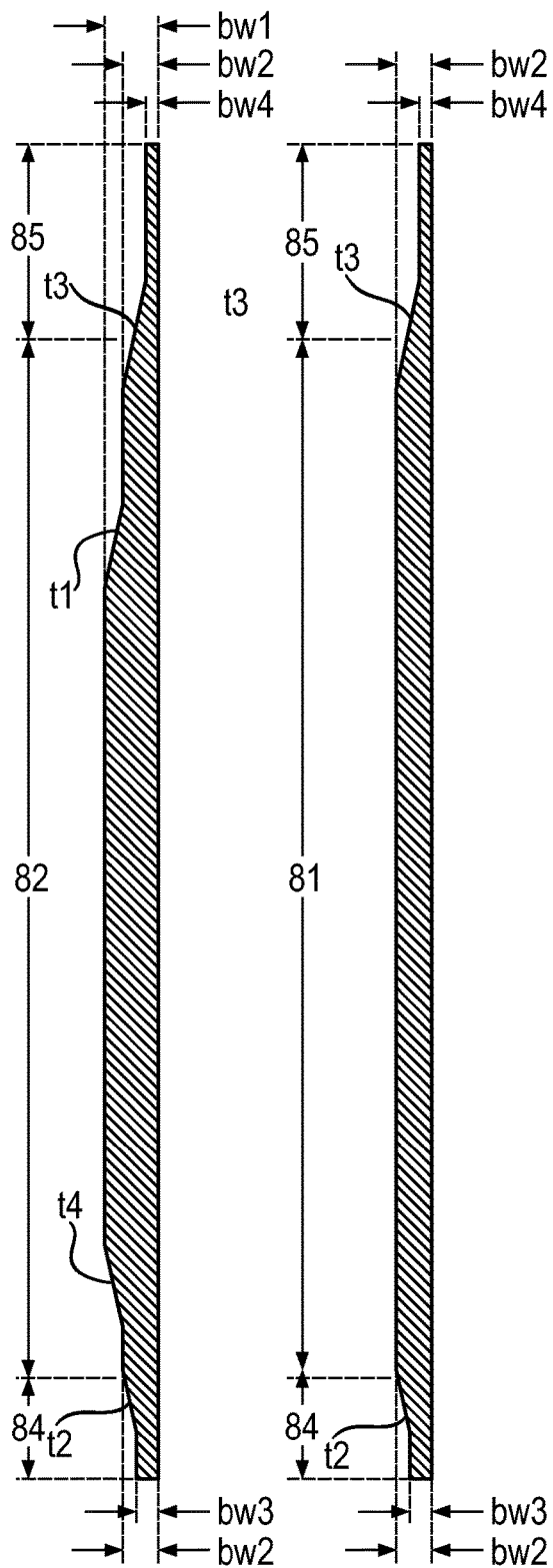
Fig. 20   Fig. 21   Fig. 22

ABSORBENT ARTICLE WITH A DISTRIBUTION LAYER COMPRISING CHANNELS

This application is a divisional of U.S. application Ser. No. 15/477,408, filed Apr. 3, 2017, which claims priority to European Patent Application No. 16167640.8, filed Apr. 29, 2016, the entire disclosures of both of which are incorporated herein by reference.

FIELD OF THE INVENTION

The invention relates to personal hygiene absorbent articles such as, but not limited to, baby diapers, training pants, feminine pads or adult incontinence products. The invention is in a first aspect directed to an improved distribution layer that efficiently uses a fibrous distribution material.

BACKGROUND OF THE INVENTION

Absorbent articles for personal hygiene are designed to absorb and contain body exudates, in particular large quantity of urine. These absorbent articles typically comprise several layers that provide different functions, for example a topsheet for quickly acquiring the fluid and feel soft on the wearer's skin, a backsheet for protection the wearer's clothes, an absorbent core for retaining fluid, and an acquisition or distribution layer between the topsheet and the absorbent core for pulling the liquid away from the topsheet and bringing it into the absorbent core.

Absorbent cores traditionally comprise as absorbent material a blend of cellulose fibers with superabsorbent polymer (SAP) particles, also called absorbent gelling materials (AGM), see for example U.S. Pat. No. 5,151,092 (Buell). Absorbent articles having cores consisting essentially of SAP without cellulose fibers as absorbent material (so called "airfelt-free" cores) have been more recently proposed. For example WO2008/155699 (Hundorf) discloses absorbent cores with a patterned layer of SAP immobilized by a net of fibrous thermoplastic adhesive material deposited over the layer of SAP. The fibrous thermoplastic material helps maintaining the SAP in position within the absorbent core prior to and during use of the article, without substantially restricting the ability of the SAP to absorb large volumes of urine. More recently, WO2012/170783 (Hundorf et al.) discloses absorbent cores comprising absorbent material having a basis weight that varies across the absorbent core. WO2012/170778 (Rosati et al.) discloses absorbent structures that comprise superabsorbent polymers, optionally a cellulosic material, and at least a pair of substantially longitudinally-extending channels (see also WO2012/170779, WO2012/170781 and WO2012/170808). The core wrap can be adhesively bonded through the channels to form a channel bond. The integrity of the channel bonds may be at least partially maintained in wet state.

It is also known to provide an intermediate layer between the topsheet and the absorbent core. These intermediate layers are designed to quickly acquire and/or distribute the fluid away from the topsheet and bring it into the core. These intermediate layers are sometimes called "wicking layer", "surge layer", "acquisition layer" or "distribution layer". These intermediate layers typically do not comprise superabsorbent material.

Absorbent articles having only one of these intermediate layers are known. WO94/23761 (Payne) for example discloses an acquisition layer comprising an homogeneous composition of hydrophilic fibrous material comprising stiffened, twisted, and curled cellulose fibers and having a densified distribution zone. Other examples are found in U.S. Pat. Nos. 5,486,166 and 5,490,846 (Bishop). Articles having two intermediate layers or more, in particular an acquisition layer having a high capillarity which pulls the fluid quickly away from the topsheet and a distribution layer having a larger void area to distribute the fluid over a large surface over the core, are also known. For example WO2014/93323 (Bianchi et al.) discloses an absorbent article with a profiled acquisition-distribution system. Other exemplary references disclosing such intermediate layers are US2008/0312621 and US2008/0312622 (both Hundorf et al.), WO99/17679 (Everett et al.). Absorbent articles comprising channels in the absorbent core and partially overlapping channels in a liquid management system have been more recently disclosed in WO2015/31225, WO2015/31229, WO2015/31243, WO2015/31256 (Roe et al.).

While the known absorbent articles can have good overall properties, there is a continuous need to improve comfort, fit and efficiency of the current articles while reducing the usage of raw material to keep the price of manufacture as low as possible. The present invention addresses these problems.

SUMMARY OF THE INVENTION

The present invention is directed to an improved absorbent article having a fibrous distribution layer. The article extends in a longitudinal direction parallel to a longitudinal axis and a transversal direction perpendicular to the longitudinal direction. The absorbent core comprises a fluid permeable topsheet on the wearer-facing side, an absorbent core comprising an absorbent material, in particular a superabsorbent polymer material, a fluid-impermeable backsheet on the garment-facing side and a distribution layer between the topsheet and the absorbent core. The distribution layer has:

- a first and second longitudinally-extending channels substantially free of fibrous material; wherein the first channel is on one side of the longitudinal axis and the second channel is on the other side of the longitudinal axis;
- a central area comprising fibrous material disposed between the first and second longitudinally-extending channels at an average central area basis weight;
- a first and second lateral areas comprising fibrous material and disposed transversally outwardly of the first and second channel respectively, wherein the first and second lateral areas have an average lateral areas basis weight.

In a first aspect of the invention, the average central area basis weight differs from the average lateral areas basis weight in the first and second lateral areas by at least 50 $g/m^2$ (grams per square meter or "gsm"). The average central area basis weight may be higher or lower than the average lateral areas basis weight of the first and second lateral areas. The relative amount of distribution material can be adapted to the types of absorbent articles considered, including the type of absorbent cores disposed underneath the distribution layer. For most absorbent articles, the higher average basis weight may typically range from 150 $g/m^2$ to 450 $g/m^2$, and the lower average basis weight may typically range from 50 $g/m^2$ to 300 $g/m^2$.

In a second aspect, the distribution layer comprises a first region having a first basis weight (bw1) and a second region having a second basis weight (bw2), wherein the first basis weight and the second basis weight differ by at least 20 g/m², advantageously by at least 50 g/m². The first region of first basis weight and the second region of second basis weight are present in different areas of the distribution layer but in a same longitudinally-extending transversal section of the distribution layer where the channels are present. The length of this transversal section may in particular range from 30% to 100% of the length of the channels, thus providing a CD profiling in at least 30% of the length of the channels up to 100%. The region of first basis weight may for example be a region of higher basis weight comprised in the central area of the distribution layer, and the region of second basis weight may be comprised in the lateral areas, both regions being comprised in the same longitudinally extending transversal section of the core. This is for example illustrated in FIGS. 4-7. Alternatively, the second region may be of lower basis weight bw2 and may be comprised in the central area while the first region is comprised in the lateral areas, both first and second regions being comprised in the same longitudinally extending transversal section of the distribution layer. This is for example illustrated in FIGS. 13-15. There may be of course further regions of different basis weight (bw3, bw4). The first aspect may be of course combined with the second aspect or may be used independently of the second aspect.

The distribution layer may in particular be used with an absorbent core having channel-forming areas that are at least partially superposed with the channels of the distribution layer. The absorbent core may thus comprise a central absorbent zone and lateral absorbent zones defined relative to the channel-forming areas of the core. The central absorbent zone and the lateral absorbent zones may advantageously have different average basis weight. In this way, the higher basis weight area of the distribution layer may match the higher basis weight zone of the absorbent core, and likewise for the lower basis weight area. The absorbent core may be free of cellulose fibers.

The distribution material may be typically distributed in regions having different pre-determined basis weight. These regions may overlap different areas of the distribution layer. These regions may be typically separated by continuous transition areas in the longitudinal direction, whereas the channels may act as discontinuous transition areas between these regions of different basis weight in the transversal direction, at least along a portion of the length of the channels. It may be advantageous to have a relatively high amount of distribution material in the central area at the P point of the article, which is defined as the point on the longitudinal axis situated at a distance of 0.30 of L" from the front edge of the article, L" being the length of the article measured along the longitudinal axis. The distribution material may be comprised of cellulose fibers, in particular cross-linked cellulose fibers, but other materials are possible, in particular fibrous materials having a Water Retention Value of from 2 to 60, as measured by Water Retention Value Procedure described herein.

The first and second channels may be at least partially curved or angled so that the width of the central area varies at least along a portion of the length of the distribution layer. Alternatively the first and second channels may be straight and oriented parallel to the longitudinal axis. This and further aspects will now be further described in the following description.

BRIEF DESCRIPTION OF THE DRAWINGS

FIG. 9 is a schematic transversal cross-section of the core of FIG. 8.

FIG. 10 is a schematic longitudinal cross-section of the core showing an optional dual absorbent layer construction.

FIG. 11 is a schematic close-up view of a section of FIG. 10.

FIGS. 17-19 show an alternative distribution layer taken in isolation.

FIGS. 20-22 show an alternative distribution layer taken in isolation.

DETAILED DESCRIPTION OF THE INVENTION

General Description of an Absorbent Article

Figure 1:
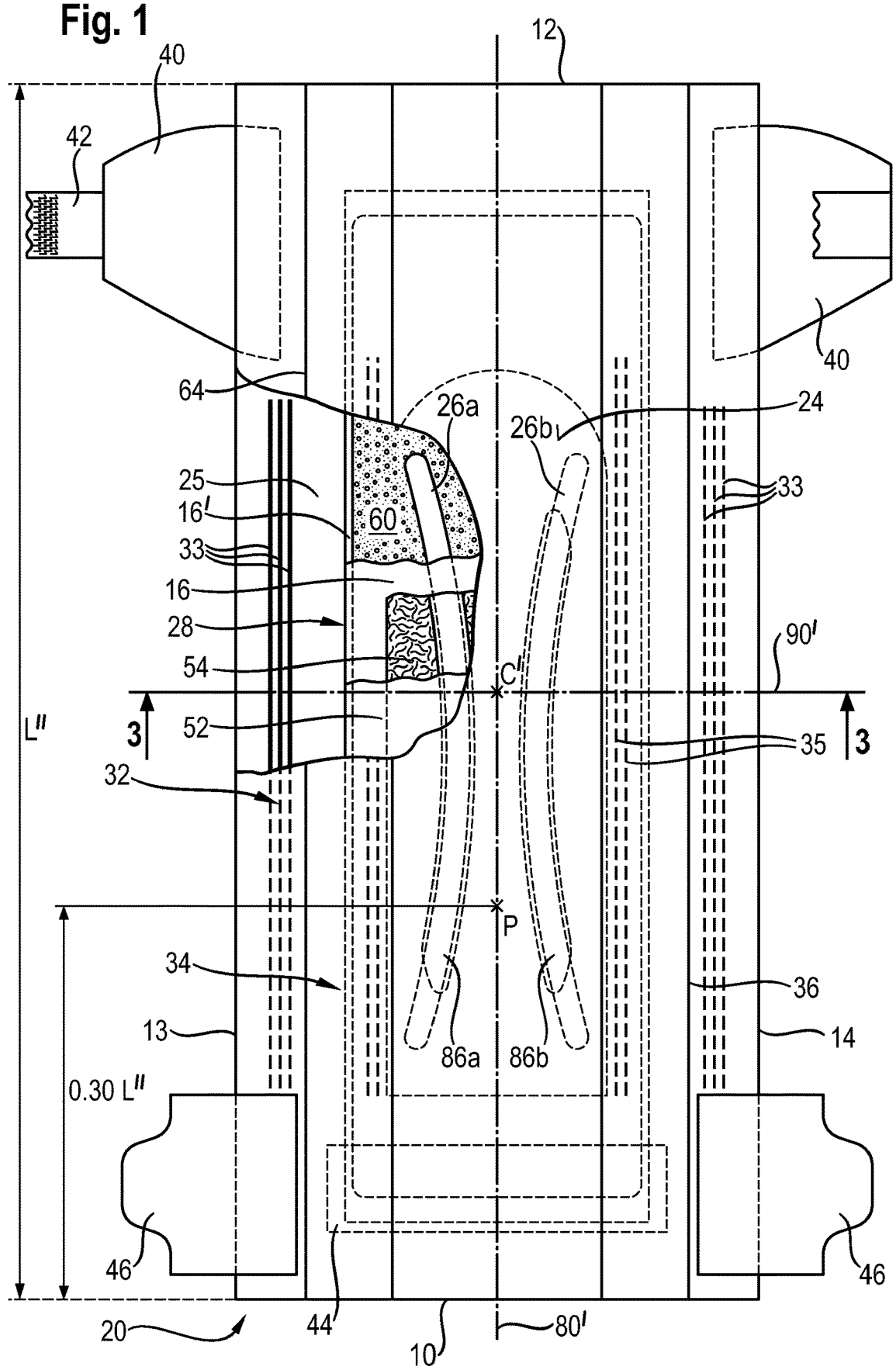
FIG. 1 is a top view of an exemplary article of the invention in the form of a taped diaper which has been pulled flat, with some layers partially removed.
Figure 2:
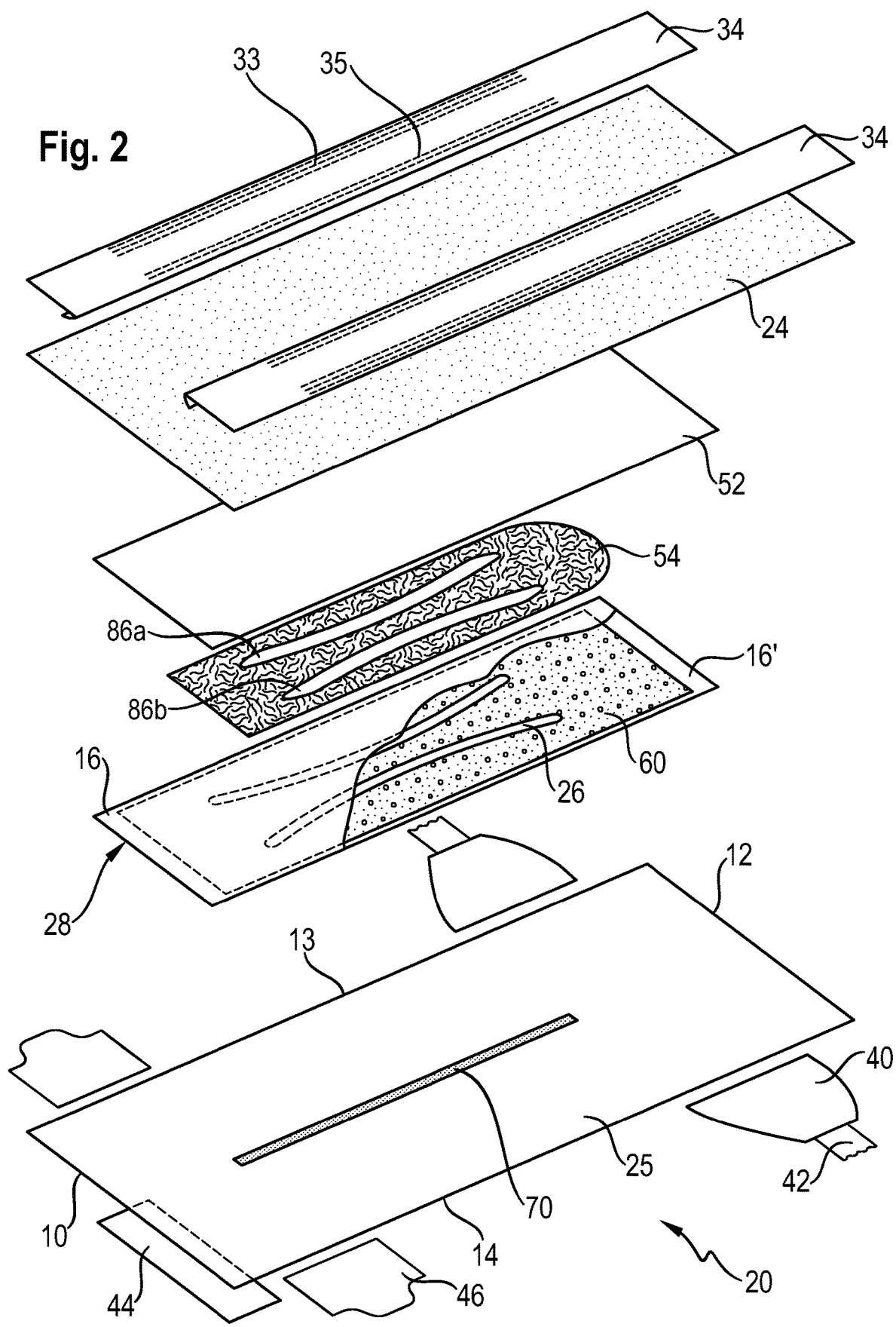
FIG. 2 shows an exploded view of the taped diaper of FIG. 1.
Figure 3:
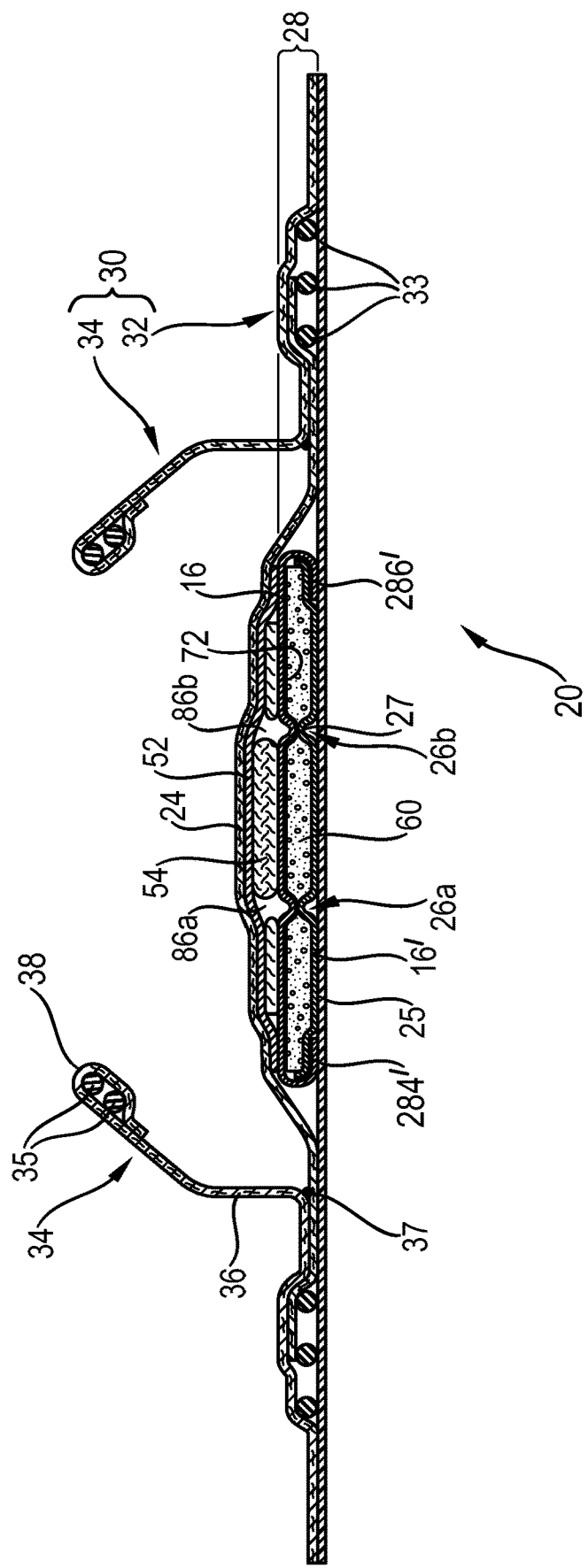
FIG. 3 shows a transversal cross-section of the diaper of FIG. 1.
Figure 24:
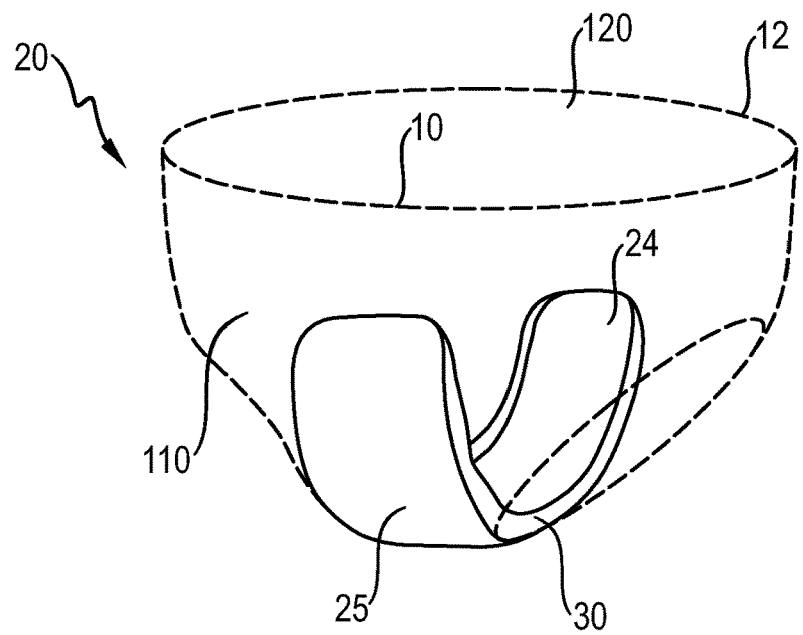
FIG. 24 schematically shows an article in the form of a pant.
Figure 25:
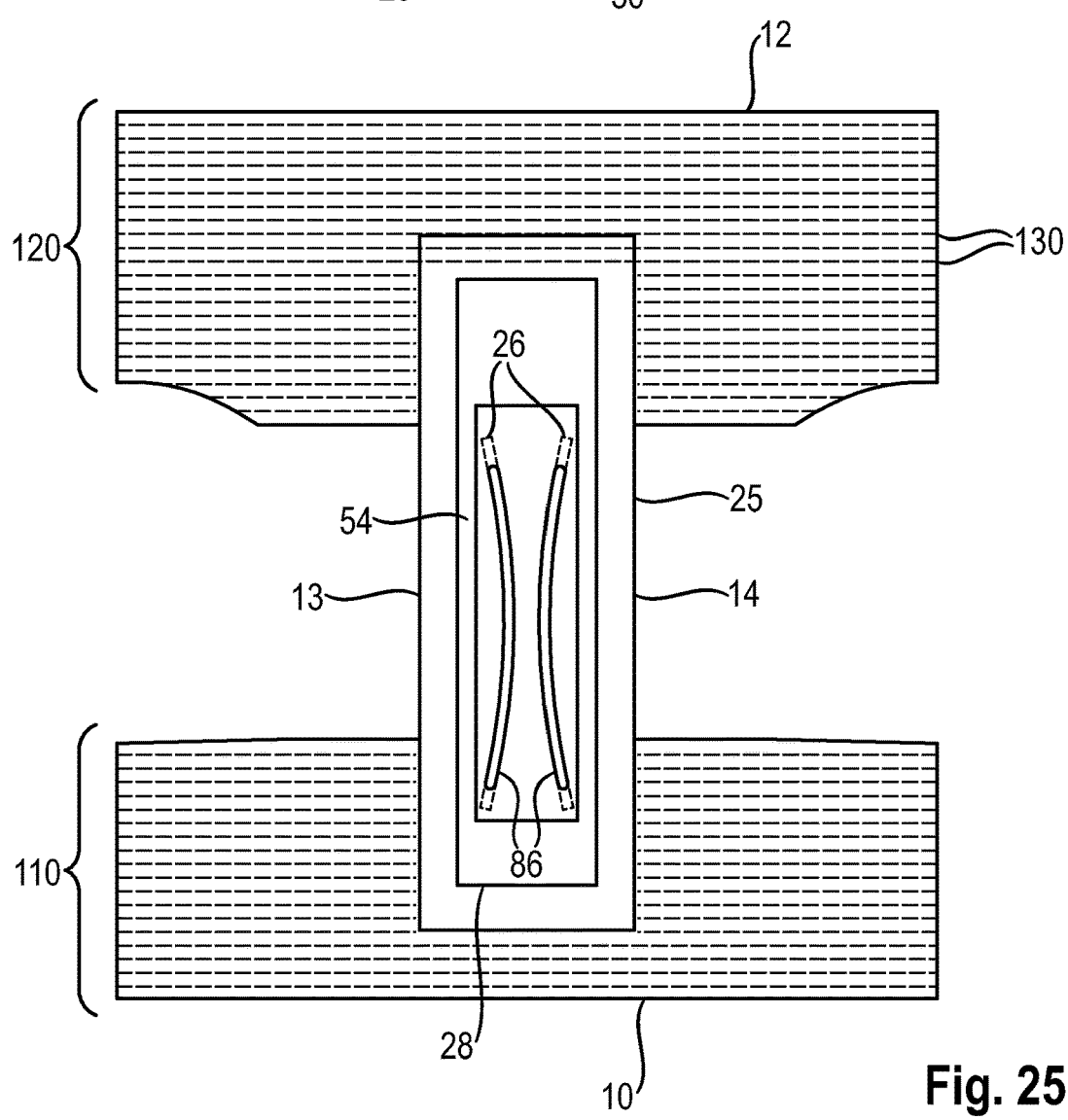
FIG. 25 schematically shows a pant article with the side seams opened.

An exemplary absorbent article according to the invention in the form of a baby taped diaper 20 is represented in FIGS. 1-3. FIG. 1 is a top plan view of the exemplary diaper in a flat-out state, with portions of the structure being cut-away to more clearly show the construction of the diaper. FIG. 2 is an exploded view showing the different layers of the diaper of FIG. 1. FIG. 3 is transversal cross-sectional view of the diaper 20 taken along line 2-2 in FIG. 1. This diaper 20 is shown for illustration purpose only, as the invention may be used for making a wide variety of diapers or other absorbent articles such as training pants, adult incontinence pants or feminine sanitary pads. FIGS. 24-25 for example schematically show a pant type absorbent article that may also use the invention.

The absorbent article 20 comprises a liquid permeable topsheet 24, a liquid impermeable backsheet 25 and an absorbent core 28 between the topsheet and the backsheet. The absorbent article represented also comprises an acquisition layer 52 directly underneath the topsheet and a distribution layer 54 according to invention. The acquisition layer 52 is optional. The distribution layer 54 has a pair of longitudinally-extending channels 86a,b which are substantially free of absorbent material. The distribution layer 54 will be further discussed in details in the next section. Other typical diaper components are represented such as elasticized gasketing cuffs 32, upstanding barrier leg cuffs 34, fastening tabs 42 and landing zone 44, an urine indicator 70. These further components will be discussed in more details further below. The absorbent article may also comprise other typical components, which are not represented in the Figures, such as a back elastic waist feature, a front elastic waist feature, transverse barrier cuffs, a lotion application, etc.

The absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article is notionally divided by a longitudinal axis 80' extending along a longitudinal direction from the middle of the front edge to the middle of the back edge of the article and dividing the article in two substantially symmetrical halves relative to this axis, when viewing the article from the wearer-facing side in a flat out configuration, as exemplarily shown in FIG. 1. This axis 80' may typically be concomitant with the longitudinal axis 80 of the core. If some parts of the article are under tension due to elasticized components, the article may be typically flattened using clamps along the periphery of the article and/or a sticky surface, so that the article can be pulled taut so as to be substantially flat. Closed articles such as training pants or adult incontinent pants may be cut open along the side seams to apply them on a flat surface (as illustrated on FIG. 25). Unless otherwise indicated, dimensions and areas disclosed herein apply to the article in this flat-out configuration.

The article has a length L" as measured along the longitudinal axis 80' from the back edge to the front edge. The absorbent article can also be notionally divided by a transversal axis 90' into a front region and a back region of equal length measured on the longitudinal axis, when the article is in such a flat state. The transversal axis 90' is perpendicular to the longitudinal axis 80' and placed at half the length of the article. The intersection of the longitudinal axis 80' and the transversal axis 90' is defined herein as the centerpoint C' of the article. The P point is further defined herein as the point on the longitudinal axis situated at a distance of 0.30 of the length of the article (L") from the front edge of the article. The P point typically corresponds in many articles to a zone of relatively high volume of fluid insult.

The absorbent core represented comprises a pair of channel-forming areas 26, which may be substantially free of absorbent material and through which the top side of the core wrap is bonded to the bottom side of the core wrap. The absorbent core can alternatively comprise channels without core wrap bonds, or may be devoid of channels or channel-forming areas. However the channels of the distribution layer according to the invention can advantageously cooperate with such channel-forming areas present in an absorbent core, especially when these are at least partially superposed with the channels of the distribution layer as illustrated in FIG. 3.

The topsheet 24, the backsheet 25, the absorbent core 28 and the other article components may be assembled in a variety of well-known configurations, in particular by gluing, fusion and/or pressure bonding. The topsheet 24 and the distribution layer 52, if present, may be attached to the top side 288 of the absorbent core through the channel of the distribution layer if desired (not shown in FIG. 3) for example by gluing. The absorbent article is preferably thin. The article may for example have a caliper of from 1.0 mm to 8.0 mm, in particular from 1.5 mm to 6.0 mm, at the centerpoint C' as measured using the Absorbent Article Caliper Test described below.

Distribution Layer 54

The absorbent article comprises a distribution layer 54 between the topsheet 24 and the absorbent core 28. There may be other layers between the distribution layer and any of the topsheet and the absorbent core, for example an acquisition layer 52. The function of the distribution layer is to spread the insulting fluid liquid over a larger surface within the article so that the absorbent capacity of the core can be more efficiently used. The distribution layer is made of a fibrous material typically based on synthetic or cellulosic fibers and has a relatively low density. The fibrous material may be manufactured by air-laying the fibers on a drum comprising several molds each having the required depth profile for the desired fibrous material configuration. The formed distribution layer can then be directly un-molded onto another component of the article such as nonwoven and then integrated with the rest of the chassis of the article. When a nonwoven acquisition layer 52 is present in the article, the distribution layer may be for example deposited on this acquisition layer, the two layers being further joined to absorbent core and the rest of the article, as is known in the art. The fibrous material used to make the distribution layer may have a Water Retention Value of from 2 to 60, in particular from 3 to 40, more particularly from 4 to 20, as measured by the Water Retention Value Procedure described further below. The density of the distribution layer may vary depending on the compression of the article, but may typically range from 0.03 g/cm$^3$ to 0.25 g/cm$^3$, in particular from 0.05 g/cm$^3$ to 0.15 g/cm$^3$, measured at 0.30 psi (2.07 kPa), and may be for example measured at the centerpoint C' or the P point. A particularly preferred distribution material comprises or consists of cross-linked cellulose fibers, as will be detailed further below, but other typical distribution materials can also be used.

The distribution layer of the invention comprises a first longitudinally-extending channel 86a substantially free of fibrous material on one side of the longitudinal axis, and a second longitudinally-extending channel 86b on the other side of the longitudinal axis. These channels define between them a central area 82 comprising fibrous material. The central area has an average central area basis weight. The channels further define a first lateral area 81 comprising fibrous material disposed transversally outwardly of the first channel 86a and a second lateral area 83 comprising fibrous material disposed transversally outwardly of the second channel 86b. The central and the lateral areas thus have about the same length, which is the length of the channels. The basis weight in the first lateral area is typically about equal to the basis weight in the second lateral area because the article is normally symmetrically arranged relative to the longitudinal axis. The distribution layer also comprises a front area 84 disposed longitudinally in front of the channels 86, and a back area 85 disposed longitudinally behind the channels 86.

Figure 4:
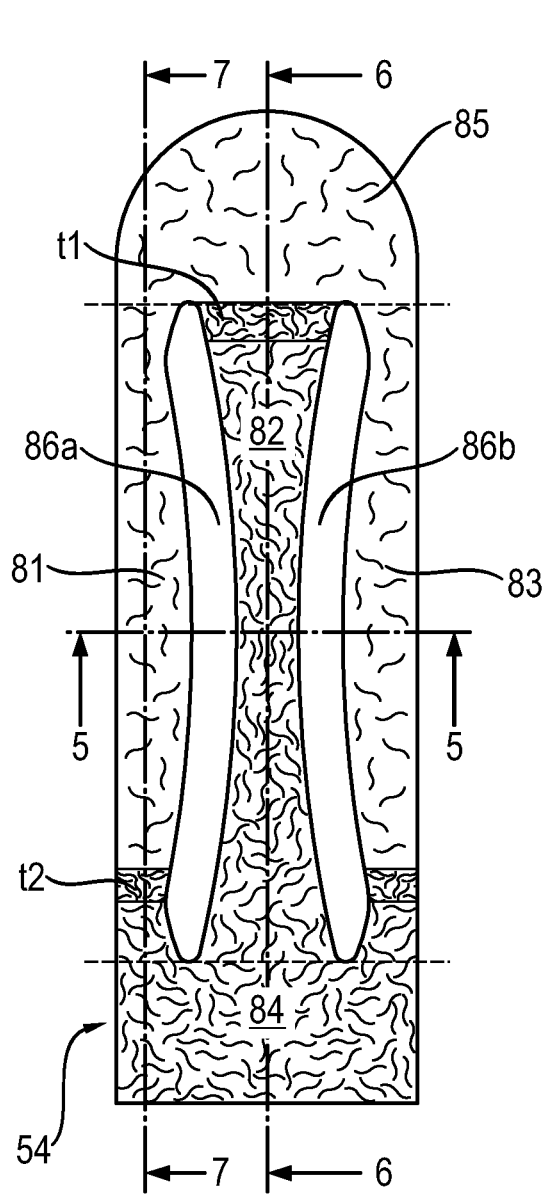
FIG. 4 shows a top view of the distribution layer of the diaper of FIGS. 1-3 in isolation.

The channel may be typically at least partially curved. In particular the channels may be concave (inwardly curved) towards the longitudinal axis 80' as illustrated in FIG. 4. Alternatively, it is not excluded that the channels may be partially or entirely straight, and in particular longitudinally oriented parallel to the longitudinal axis 80', or curved in the other direction. The channels are typically disposed as one or more symmetrical pair(s) relative to the longitudinal axis, and are spaced apart from one another over their whole longitudinal dimension. The shortest spacing distance between the channels may be for example at least 5 mm, or at least 10 mm, or at least 16 mm. It is however not excluded that the channels may be joined together, for example at their front or back extremities. Furthermore, in order to reduce the risk of fluid leakages, the channels optionally do not extend up to any of the edges of the distribution layer, and are therefore surrounded by and fully encompassed within the distribution layer. The smallest distance between a channel and the closest edge of the distribution layer may be at least 5 mm.

It has been suggested in the past to profile the distribution layer in the longitudinal direction and to provide two material-free channels in the distribution layer on either side of the longitudinal axis (see e.g. WO2014/93323, Bianchi et al. and WO2015/31225, Roe et al). The present invention now provides a distribution layer having a profiled basis weight configuration in the transversal direction. According to a first aspect of the invention, the average central area basis weight differs from the average lateral areas basis weight by at least 50 g/m$^2$ (grams per square meter, or gsm), in particular at least 60 g/m$^2$, or at least 70 g/m$^2$, or at least 80 g/m$^2$. The central area may be the area having the higher average basis weight relative to the first and second lateral areas. This will be exemplified when discussing for example the distribution layer of FIGS. 4-7. Alternatively, the average central area basis weight may be at least 50 g/m$^2$, in particular at least 60 g/m$^2$, or at least 70 g/m$^2$, or at least 80 g/m$^2$ lower than the average lateral areas basis weight. This is exemplified for example in the distribution layer of FIGS. 13-15. For most absorbent articles, the average basis in the higher basis weight area may typically range from 150 g/m$^2$ and 300 g/m$^2$ and the average basis weight in the lower basis weight area would be between 50 g/m$^2$ and 200 g/m$^2$. For some articles like adult incontinence products having to deal with relatively high amount of fluid, these values may be higher. The average basis weight in the higher basis weight area may also range from 150 g/m$^2$ and 450 g/m$^2$ and the average basis weight in the lower basis weight area would be between 50 g/m$^2$ and 300 g/m$^2$ for these products.

The average basis weight in each area of the distribution layer can be measured experimentally by removing and weighing the fibrous material in the area considered (central area or both lateral areas) and dividing this weight by the surface of the area considered. The surface of the area can be determined by taking a picture and analyzing it using any commercial image analysis software, or by any other conventional methods. The channels and any other areas which are substantially free of fibrous distribution material are disregarded for calculating the average basis weight of the different areas. It is unlikely that the average basis weights in the first and second lateral area substantially differs, but in any case the combined weight of the distribution material if both areas and the combined surface of both lateral areas is used to determine the average lateral areas basis weight.

Independently of the relation between the basis weigh of the central and the lateral areas, it may be further advantageous that the basis weight of the distribution material measured at the P point (P) is maximum relative to the rest of the distribution layer. By maximum, it is meant that the distribution layer does not comprise another point having a higher basis weight, but of course there may be other point or regions in the distribution layer having the same basis weight. The P point may in particular belong to a region of higher basis weight (bw1) in the distribution layer. The P point is defined herein as the point of the distribution layer on the longitudinal axis disposed at a distance of 0.30 of the length of the article (L") from the front edge 10 of the article. The basis weight at the P point or on any the other regions of the distribution layer can be typically directly determined from the manufacturer's specification of the layer making machine. If the specification is not known, the local basis weight at the P point may be measured by taking a circular sample having a diameter of 10 mm and centered on the P point. The distribution material in this area is weighed and divided by the surface area of the circle to provide the local basis weight value.

The basis weight transition in the transversal direction between regions of the distribution layer having different basis weight can be typically discontinuous (in other word discrete). The channels in the distribution layer can act along at least a portion of their length as boundaries between regions of the distribution layer having different basis weight. The profiling of the distribution layer in the transversal direction can be used to provide an improvement of the performance of the article and/or a cost reduction. Of course, the distribution layer may still be profiled in the longitudinal direction in each area. This may be advantageous to have more distribution material in regions of the article that are more susceptible to receive fluid for example. The basis weight transition in the longitudinal direction between regions of the distribution layer having different basis weight can typically be continuous. This means that may typically be transition zones in the longitudinal direction as will be exemplified further below.

The general shape of the distribution layer as seen from above may be generally rectangular, as is typical in the art, but may be also shaped (that is non-rectangular), for example having a bullet shape as illustrated on FIG. 4 with a back edge that is rounded, or may have a tapered outline in its middle as illustrated on FIG. 20. The different configurations can be used to maximize the efficiency of the distribution layer for different applications.

The distribution layer is a fibrous layer. The distribution layer may be a nonwoven material comprising fibers that are bonded to another so that the layer has a strong integrity and may be manipulated independently of a substrate. However the distribution layer is more typically not a nonwoven layer, but preferably comprises or consists of loose fibers with no or weak intra-fiber bonds that are deposited on a supporting substrate at varying basis weight to form a profiled distribution. A typical example of distribution material comprises or consists of cross-linked cellulose fibers. The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance against the compression in the product packaging or in use conditions, e.g. under baby weight.

Exemplary chemically cross-linked cellulosic fibers suitable for a distribution layer are disclosed in U.S. Pat. Nos. 5,549,791, 5,137,537, WO95/34329 or US2007/118087. Exemplary cross-linking agents include polycarboxylic acids such as citric acid and/or polyacrylic acids such as acrylic acid and maleic acid copolymers. For example, the cross-linked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form. The C2-C9 polycarboxylic acid cross-linking agent may be selected from the group consisting of:

aliphatic and alicyclic C2-C9 polycarboxylic acids having at least three carboxyl groups per molecule; and
aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid cross-linking agent is separated from a second carboxyl group by either two or three carbon atoms. The fibers may have in particular between about 1.5 mole % and about 6.0 mole % cross-linking agent, calculated on a cellulose anhydroglucose molar basis, reacted therewith in the form of intrafiber ester crosslink bonds. The cross-linking agent may be selected from the group consisting of citric acid, 1, 2, 3, 4 butane tetracarboxylic acid, and 1, 2, 3 propane tricarboxylic acid, in particular citric acid.

Polyacrylic acid cross-linking agents may also be selected from polyacrylic acid homopolymers, copolymers of acrylic acid, and mixtures thereof. The fibers may have between 1.0 weight % and 10.0 weight %, preferably between 3 weight % and 7 weight %, of these cross-linking agents, calculated on a dry fiber weight basis, reacted therewith in the form of intra-fiber crosslink bonds. The cross-linking agent may be a polyacrylic acid polymer having a molecular weight of from 500 to 40,000, preferably from 1,000 to 20,000. The polymeric polyacrylic acid cross-linking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid cross-linking agent.

The distribution layer comprising cross-linked cellulose fibers may comprise other fibers, but this layer may comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

Figures 6, 7:
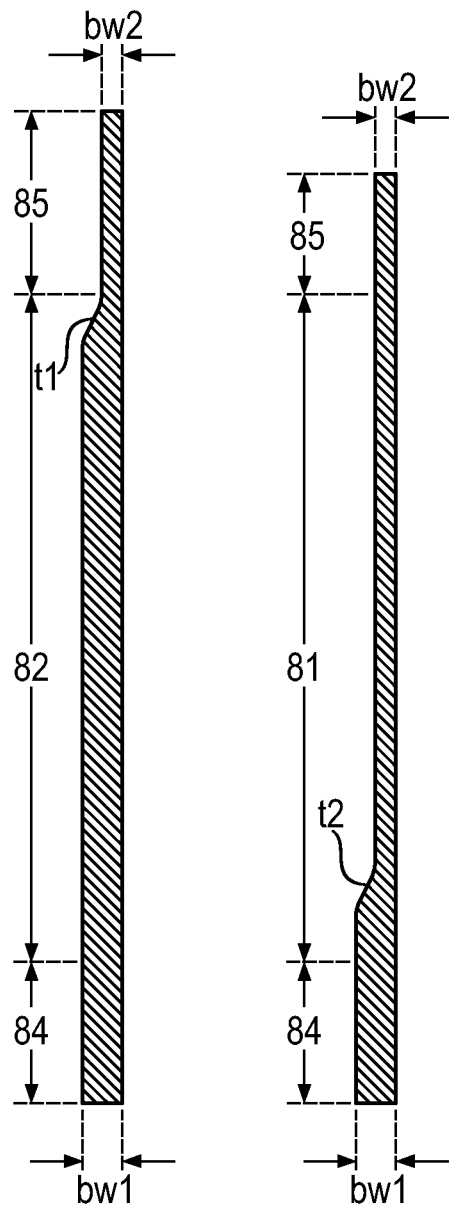
FIGS. 6 and 7 shows two longitudinal cross-sections of the distribution layer of FIG. 4.
Figure 5:
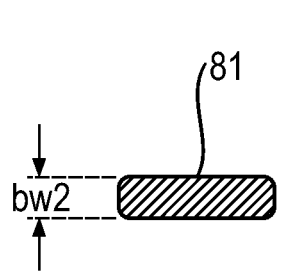
FIG. 5 shows a transversal cross-section of FIG. 4.

FIGS. 4-7 illustrate a first example of distribution layer represented in isolation without the substrate such as an acquisition layer or the core cover on which it may be deposited. FIG. 4 shows a top, planar view of the distribution layer. The front edge of the distribution layer is the straight edge and the back edge of the distribution layer is the rounded edge. The rounded edge oriented toward the back of the article in the finished product. FIG. 5 shows schematically a transversal cross-section through the middle of the distribution layer. FIG. 6 shows a longitudinal cross-section of the distribution layer parallel to the longitudinal axis of the article and FIG. 7 shows a longitudinal cross-section through the first lateral area 81.

In this example, the fibrous material is deposited in a first region having a relatively high basis weight bw1, and a second region having a relatively low basis weight bw2. The region of higher basis weight bw1 extends across the whole of the front area 84 of the distribution layer, most of the central area 82 and to a small at extent the front part of the lateral areas 81, 83. The region of lower basis weight bw2 is present through most of the length of the lateral areas 81, 83 and the back area 85. These regions of constant basis weight are separated by gradual transition zones t1, t2 in the longitudinal direction. These transition zones may be relatively short compared to the rest of the layer. On the other hand, the transition is discrete in the transversal direction between the regions of the central area and the lateral areas having different basis weight, with the channels acting as boundaries serving as discrete transition zones.

These considerations may be generalized beyond this example for any distribution layers according to the invention. The length (measured in the longitudinal direction) of the longitudinally-extending transversal section of the core where both regions of different basis weight are present in the areas of the channels may in particular be range from 30% to 100% of the length of the channels (L'). The regions of higher basis weight may also be alternatively on the lateral areas of the distribution layer, while the region of lower basis weight being on the central area. This is for example illustrated in FIG. 13.

The fibrous material of the distribution layer may also be deposited in more than two regions of different basis weight, and that may extend to different areas. The regions of different basis weight can be separated longitudinally by gradual transition zones, while the transition may be discrete in the transversal direction between the regions across at least along a portion of the length of the channels, with the channels acting as boundaries serving as discrete transition zones.

The dimensions and basis weight values for the different areas, regions and channels of the distribution layer can be of course adapted for the different types of absorbent articles considered. Typically, the more fluid needs to be distributed, the higher the basis weight is required to provide the performance desired. To give purely exemplary values, a size 4 baby diaper (recommended for babies weighing 7-18 kg) may have for example a higher basis weight bw1 of 220 gsm and a lower basis weight of 120 gsm, but other values are of course possible. Typically, the distribution layer may comprise a first region having a first basis weight (bw1) and a second region having a second basis weight (bw2), wherein the first basis weight and the second basis weight differ by at least 20 g/m$^2$, in particular at least 50 g/m$^2$, or at least 60 g/m$^2$, or at least 70 g/m$^2$, or at least 80 g/m$^2$. The first basis weight region and the second basis weight region may be typically longitudinally separated by a continuous transition area (t1, t2). Of course there may be further regions of constant basis weight.

The distribution layer as a whole (including for simplification the channel areas) may typically have an average basis weight of from 30 g/m$^2$ to 400 g/m$^2$, in particular from 100 g/m$^2$ to 300 g/m$^2$, for the whole distribution layer. Heavy adult incontinence products may for example have a higher basis weight, and smaller sizes diaper a lower basis weight. The underlying absorbent core also plays a role when deciding the shape and amount of material of the distribution layer. Typically higher amount of absorbent material in the absorbent core requires higher amount of distribution material superposed therewith and vice versa. Before discussing the further examples of distribution layer of FIGS. 17-22, an example of absorbent core will be generally described in the following section.

General Description of the Absorbent Core 28

The distribution layer may advantageously cooperate with the underlying absorbent core to provide improved performance in terms of fluid handling and/or wearing comfort. Thus before discussing other examples of distribution layers, an exemplary absorbent core and its combination with the distribution layer of FIGS. 4-7 will be briefly discussed with exemplary reference to the FIGS. 8-12. The absorbent core 28 may in particular advantageously comprise at least two longitudinally-extending areas that are substantially free of absorbent material, which are herein referred as channel-forming areas 26a, 26b. The channel-forming areas 26 may be longer or shorter than the channels 86 of the distribution layer, but advantageously the channel-forming areas of the core correspond at least along a portion of their length to the channels in the distribution layer. In this way, the fluid can be directly transferred vertically via the channels to the center of the absorbent core, as well as being spread longitudinally along its length.

An exemplary absorbent core taken in isolation is illustrated on FIGS. 8-11. As used herein, the term "absorbent core" or "core" refers to a component of an absorbent article which comprises an absorbent material contained in a core wrap. As used herein, the term "absorbent core" does not include the topsheet, the backsheet, and the distribution layer. The absorbent core has typically the most absorbent capacity of all the components of the absorbent article, and comprises all or at least the majority of superabsorbent polymer (SAP) in the article. The core typically thus consists essentially of, or consists of, the core wrap, the absorbent material and optionally adhesives. The absorbent material may consist of SAP in particulate form as exemplified in the present description but it is not excluded that other type of absorbent material may be used. The terms "absorbent core" and "core" are herein used interchangeably.

Figure 8:
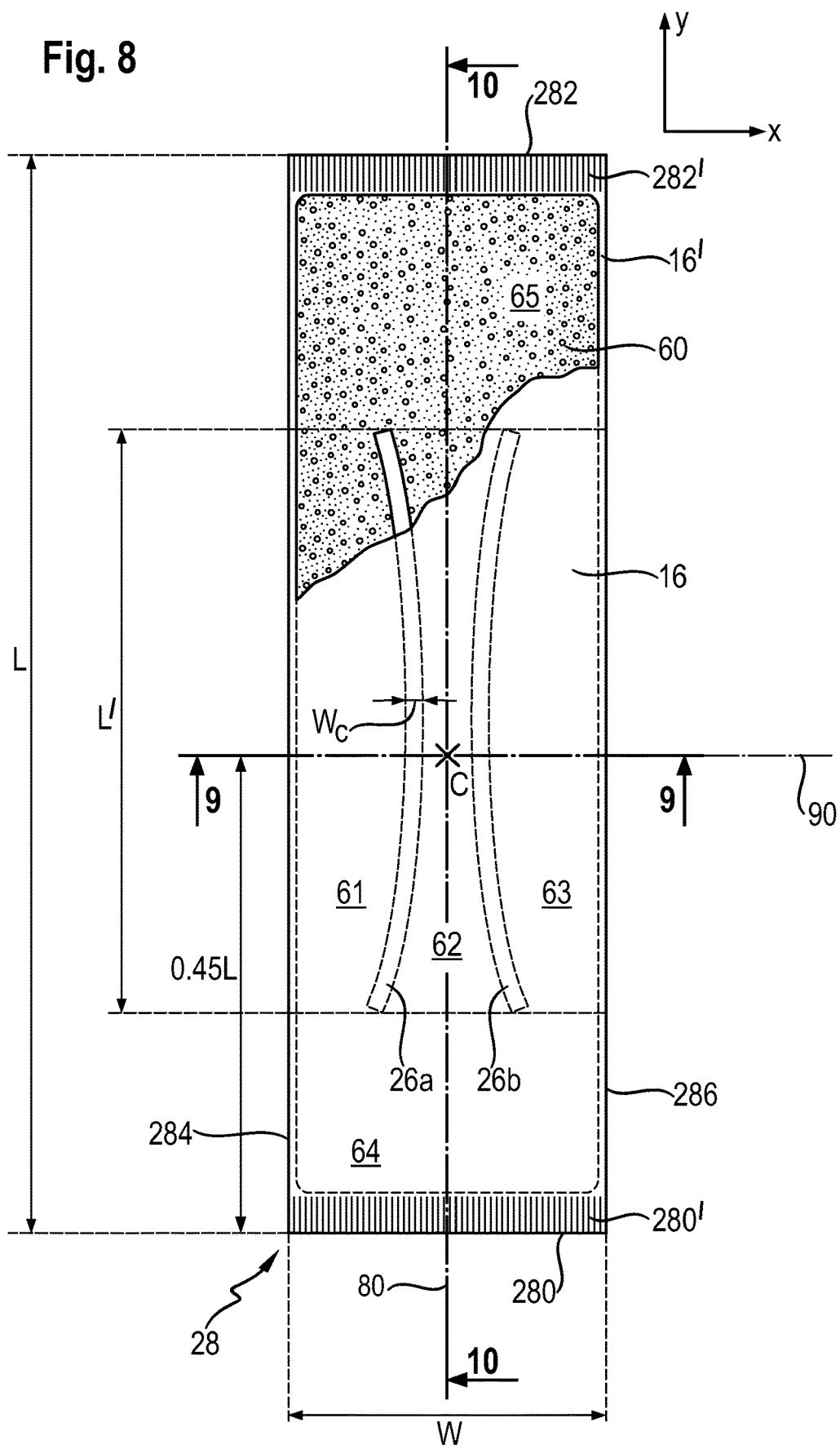
FIG. 8 is a top view of an absorbent core comprising two curved channel-forming areas, with the top layer of the core wrap partially removed.

The absorbent core may be substantially planar so that it can be laid flat on a surface. The absorbent core may also be typically thin and conformable, so that it can also be laid on a curved surface for example a drum during its making process or stored as a continuous roll of stock material before being converted into an absorbent article. FIGS. 8-11 schematically show an absorbent core as known from the prior art, e.g. as in WO2012/170,778 (Rosati et al.). The absorbent cores of the invention may comprise the same basic features as this absorbent core. For ease of discussion, the exemplarily absorbent core of FIG. 8 is represented in a flat state and extending in a plane along a transversal direction (x) and a longitudinal direction (y). Unless otherwise indicated, dimensions and areas disclosed herein apply to the core in this flat-out configuration. The same applies to an absorbent article, as exemplarily represented in FIG. 1, in which the core is integrated. For ease of discussion, the absorbent cores and articles of the invention will be discussed with reference to the Figures and the numerals referred to in these Figures, however these are not intended to limit the scope of the claims unless specifically indicated.

The outline of the absorbent core is typically defined by the core wrap. The core wrap may comprise two individual substrates 16, 16' as illustrated in the Figures, but it is also common and possible to have a single substrate forming the core wrap. The absorbent core typically comprises a front edge 280, a back edge 282 and two longitudinally-extending side edges 284, 286 joining the front edge and the back edge. The front edge is the edge of the core placed towards the front edge 10 of the absorbent article. Typically the absorbent material 60 of the core may be advantageously distributed in somewhat higher amount towards the front edge than towards the back edge as more absorbency is typically required towards the front half of the article. Typically the front and back edges 280, 282 may be shorter than the longitudinally-extending side edges 284, 286. The absorbent core also comprises a top side 288 and a bottom side 290. The top side of the core is the side placed or intended to be placed towards the topsheet 24 of the article and the bottom side is the side placed or intended to be placed towards the backsheet 25 in the finished article. The top side of the core wrap may be typically treated to be more hydrophilic than the bottom side.

The absorbent core can notionally (i.e. virtually) comprise a longitudinal axis 80 extending from the front edge 280 to the back edge 282 and dividing the core in two substantially symmetrical halves relative to this axis, when viewing the core in the plane formed by the longitudinal and transversal direction (x, y). The absorbent core can typically be generally rectangular with a width W in the transversal direction and a length L in the longitudinal direction as measured from edge to edge, including the region of the core wrap which does not enclose the absorbent material, in particular at the front and back end seals 280', 282' when present. In case the core is not rectangular, the maximum dimension measured along the transversal direction and the longitudinal direction can be used to report the width and length of the core respectively. The width and length of the core may vary depending on the intended usage. For baby and infant diapers, the width W may for example in the range from 40 mm to 200 mm and the length L from 100 mm to 600 mm. Adult incontinence products may have higher maximum dimensions.

The transversal axis 90 of the core (also referred to as "crotch line") is defined as the virtual line perpendicular to the longitudinal axis 80 and bisecting the diaper at a distance of 0.45 of L from the front edge 280 of the absorbent core, L being the length of the core as measured from the front edge 280 in direction of the back edge 282, as shown on FIG. 8. The crotch point C of the core is herein defined as the point of intersection of these two axis. The crotch region of the core is defined herein as the region of the core extending from the transversal axis 90, i.e. at the level of the crotch point C, towards the back edge and front edge of the core by a distance of a quarter of L (L/4) in both directions for a total length of L/2. The front region and back region of the core are the remaining regions of the core towards the front and back edges of the core respectively.

The absorbent material 60 may be any conventional absorbent material used in absorbent articles. The absorbent material may consist of SAP particles immobilized by an adhesive to provide a relatively thin core. The absorbent core may thus be relatively thin, in particular thinner than conventional cores comprising cellulosic fibers. In particular, the caliper of the core (dry, i.e. before use) as measured at the crotch point (C) or at any other points of the surface of the core according to the Dry Core Caliper Test as described herein may be from 0.25 mm to 5.0 mm, in particular from 0.5 mm to 4.0 mm. However other types of absorbent material are more commonly used, the absorbent material may be in particular a mix of cellulose fibers and SAP particles.

The absorbent material 60 may be deposited within the core wrap as one layer, or as represented in FIGS. 10-11 as two absorbent layers applied on the top substrate 16 and bottom substrate 16' respectively in a pattern of land areas 75,75' separated by junction areas 76,76'. This advanced way of making cores free of cellulose fibers is for example generally disclosed in WO2008/155699. In particular, two absorbent layers having offset land 75, 75' and junction areas 76, 76' may be combined to form an absorbent material deposition area in which the absorbent material is substantially continuous, as shown in FIG. 8. If the absorbent core is made according to this process, it may further advantageously comprise a fibrous thermoplastic adhesive 74, 74' to further immobilize the absorbent material. However the absorbent cores of the present invention are not limited to a particular process for making them, and the cores of the invention may be more conventionally by air-laying a mix of cellulose fibers and superabsorbent particles on a conventional air-laying drum.

The absorbent material 60 defines an absorbent material deposition area as seen from above within the plane of the core. The deposition area may be generally rectangular as shown in the FIG. 8, or may be shaped so that it has a tapered section in the crotch region, as is known in the art in so-called shaped cores. The absorbent core may comprise within the deposition area at least a first longitudinally-extending area 26a and a second longitudinally-extending area 26b, which are substantially free of absorbent material and are each disposed on opposite side of the longitudinal axis. These areas will be designated herein as channel-forming areas 26a, 26b. The channel-forming areas may be typically mirror image of each other relative to the longitudinal axis. The top side 288 of the core wrap may be advantageously bonded to the bottom side 290 of the core wrap through these channel-forming areas 26 which are substantially free of absorbent material. The bonds 27 may be provided by an auxiliary glue 72 applied directly to the inner surface of at least one of the substrate, as illustrated in FIG. 9, and/or by any other bonding means such as fusion bonding or ultra-sonic bonding. Typically the bonds 27 may generally have the same outline and shape as the absorbent material free areas 26 in which they are contained, but may be slightly smaller to allow for a safety margin (e.g. by a few mm) as some deviations from the optimal registration may happen during high speed process. It is however not excluded that the channel bonds 27 may be provided in areas containing absorbent material, in those cases the bonds may however be substantially less strong and more easily delaminate when the absorbent material swells. The channel-forming areas 26 may be also be provided without such bonds, but then the absorbent material may relatively quickly fill into these areas so that the fluid handling properties of the channels may be relatively quickly compromised.

The two channel-forming areas 26a,b define a central absorbent zone 62 disposed between them, and a first and second lateral absorbent zones 61, 63 respectively disposed laterally outwardly of the first and second channel-forming areas. The central, first and second lateral absorbent zones comprise absorbent material. The first and second lateral absorbent zones typically extend laterally up to the longitudinal side edges 284, 286 of the absorbent core. As defined herein, the central absorbent zone 62 and the lateral absorbent zones 61, 63 do not extend beyond the longitudinal extremities of the channel-forming areas 26, and thus the central and the lateral zones typically all have the same length L' as the length of the channel-forming areas 26. The rest of the absorbent core comprising absorbent material may thus define a front absorbent zone 64 extending longitudinally forward of the front extremities of the channel-forming areas and up to the front end seal 280' and a back absorbent zone 65 extending longitudinally backward from the back extremities of the channel-forming areas to the back end seal 282' of the core.

The longitudinal axis 80 of the core is typically superposed with the longitudinal axis 80' of the article. As the absorbent material 60 swells when it absorbs a liquid such as urine, the bond 27 in the channel-forming areas 26 remain at least initially in place between the top and bottom sides of the core wrap, so that the channel-forming areas 26 form easily recognizable three-dimensional channels. These three-dimensional channels may further cooperate with the channels of the distribution layer 54 disposed above the absorbent core 28 to guide the fluid inside the core and longitudinally towards the front and back of the article.

Figure 12:
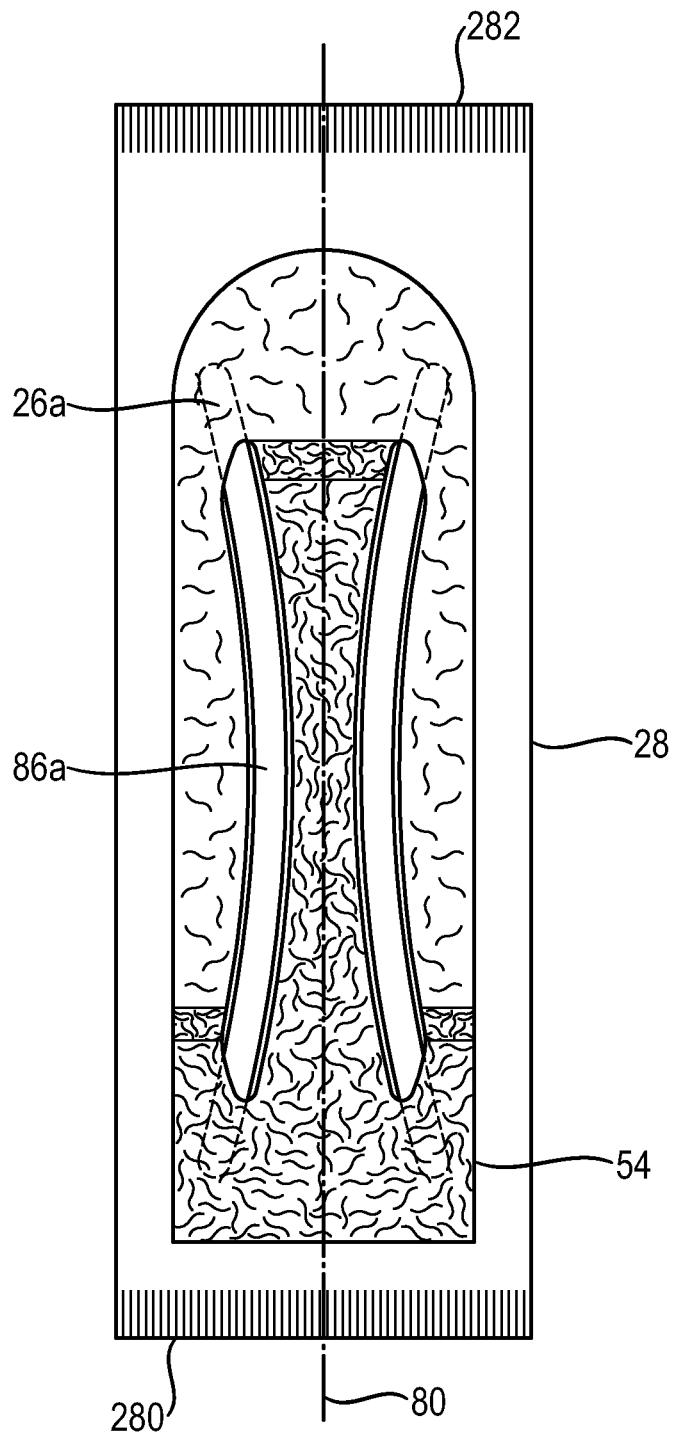
FIG. 12 shows in superposition the distribution layer of FIG. 4 with the absorbent core of FIG. 8.

The absorbent core and the distribution layer are shown superposed in FIG. 12. In this view, the channel-forming areas 26 of the core extend longitudinally further than the channels of the distribution layer 86, but the channels and channel-forming areas are otherwise superposed. Typically the absorbent core may be longer and wider than the distribution layer, so that the channel-forming areas can extend further than the channels of the distribution layer. It may be advantageous that the channels 86 or channel-forming areas 26 do not reach any of the edges of the layer in which they are formed, to reduce the risk of fluid escaping the layer. Thus the channels and channel-forming areas may be designed to stop at a distance of at least 5 mm from any edges of the layer in which they are formed. It is however also not excluded that the distribution layer may be as wide and/or as long as the absorbent core, and the channels and the channel-forming areas may have similar dimensions. It is also not excluded that the channel-forming areas 26 of the core when present are not superposed with the channels 86 of the distribution layer 54.

As illustrated in FIG. 10, the absorbent core may have a profiled distribution of material in the longitudinal direction, especially having a higher basis weight in the crotch region than in the front region, and still higher in the front region than in the back region. The absorbent core may also be profiled in the transversal direction, in particular, the absorbent core and the distribution layer may be similarly profiled in the transversal direction. Thus, the average basis weight of the absorbent material in the central absorbent zone of the core may also differ (higher or lower) than the average basis weight in the first and second lateral absorbent zones of the core. The average basis weight of the absorbent material in the central absorbent zone may differ by at least 10% than the average basis weight in the first and second lateral absorbent zones, in particular by at least 25%, or by at least 50%, or by at least 100%.

Some executions may have relatively less absorbent material in the central absorbent zone. The average basis weight of the lateral absorbent zones may then be at least 25% higher than the average basis weight in the central absorbent zone. In particular, the average basis weight of the absorbent material in the central absorbent zone may range from about 20% to about 70% of the average basis weight in the first and second lateral absorbent zones. The amount of absorbent material in the central absorbent zone may also range from about 5% to about 25% of the total amount of absorbent material in the absorbent core, and the combined amount of absorbent material in both lateral absorbent zones ranges from about 30% to 80% of the total amount of absorbent material in the absorbent core.

Alternatively, other executions may have relatively more absorbent material in the central zone. The average basis weight of the lateral absorbent zones may then be at least 25% lower than the average basis weight in the central absorbent zone. The amount of absorbent material in the central absorbent zone may then also range from about 15% to about 60% of the total amount of absorbent material in the absorbent core, and the combined amount of absorbent material in both lateral absorbent zones ranges from about 25% to 70% of the total amount of absorbent material in the absorbent core.

The average basis weight for each absorbent zone of the core can be, similarly as for the areas of the distribution layer, calculated by taking the weight of absorbent material in the zone considered and dividing this weight by the surface of this zone. The channel-forming areas and any other areas which are substantially free of absorbent material are disregarded for calculating the average basis weight of the different zones. The average basis weight may be typically the same in the first lateral absorbent zone and in the second lateral absorbent zone. If exceptionally there was a significant difference of basis weight in the first lateral zone and the second lateral zone, the weight of the absorbent material in both lateral absorbent zones is anyway added and divided by the combined surfaces of both lateral absorbent zones to provide an average value.

When the average basis weight of the central zone of the absorbent core is higher than the average basis weight of the lateral zones, the average basis weight of the distribution layer is advantageously similarly higher in the central area relative to the lateral areas of the distribution layer. Inversely, when the average basis weight of the central zone of the absorbent core is lower than the basis weight of the lateral zones of the core, the average basis weight of the distribution layer may be advantageously lower in the central area relative to the lateral area of the distribution layer. By increasing the basis weight of the distribution material in the areas superposed with the zones of the absorbent core of relatively higher basis weight, the fluid may be more efficiently distributed and absorbed by the absorbent core. For example, the distribution layer of FIGS. 4-7 having a relatively higher basis weight in the central area 82 is particularly adapted for an absorbent core having a higher basis weight of absorbent material in the central zone 62.

The total amount of absorbent material should be sufficient for the application considered. For baby diapers for example, the amount SAP should be sufficient to provide overnight dryness. For children having a weight range of 8-17 kg, as an example, the total amount of SAP in the core may be about 12 g, distributed as follows: 11.5% in the front absorbent zone, 28% in the central absorbent zone, 25% in each lateral absorbent zone, and 10.5% in the back absorbent zone (for a total of 100%). More generally, the amount of absorbent material may be for example distributed as indicated in the following Table, the percentage being reported by total weight of the absorbent material in the absorbent core:

|  | Range in weight % | In particular |
|---|---|---|
| Front absorbent zone 64 | 0*-25 | 5-20 |
| Central absorbent zone 62 | 15-60 | 20-45 |
| Lateral absorbent zone 61, 63 (combined) | 20-70 | 15-30 |
| Back absorbent zone 65 | 0*-25 | 5-15 |

*although not preferred, it is possible that the channel-forming areas extend up to the front and back edges of the absorbent core, so that the front and/or the back absorbent zones are not existent.

For absorbent cores having a relatively low amount of absorbent material in their central absorbent zones, exemplary values for the same type of baby diaper may be as follows. The total amount of SAP in the core may be about 12 g, distributed as follows: 13% in the front absorbent zone, 12% in the central absorbent zone, 32% in each lateral absorbent zone, and 11% in the back absorbent zone (for a total of 100%). The average lateral zones basis weight may be for this particular example about 500 gsm and the average central zone basis weight may be about 175 gsm. More generally, the amount of absorbent material may be for example distributed as indicated in the following Table, the percentage being reported by total weight of the absorbent material in the absorbent core:

|  | Range in weight % | In particular |
|---|---|---|
| Front absorbent zone 64 | 0*-25 | 5-20 |
| Central absorbent zone 62 | 5-25 | 10-20 |
| Lateral absorbent zone 61, 63 (combined) | 30-80 | 20-40 |
| Back absorbent zone 65 | 0*-25 | 5-15 |

*although not preferred, it is possible that the channel-forming areas extend up to the front and back edges of the absorbent core, so that the front and/or the back absorbent zones are not existent.

Other Examples of Distribution Layers

Figure 13:
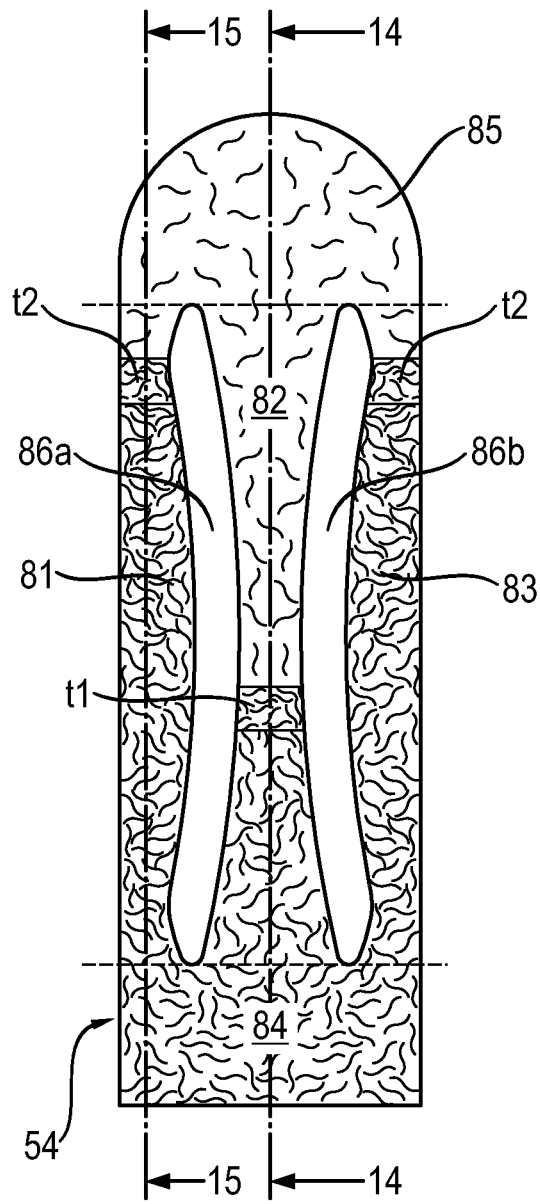
FIG. 13 shows an alternative distribution layer taken in isolation.
Figure 14:
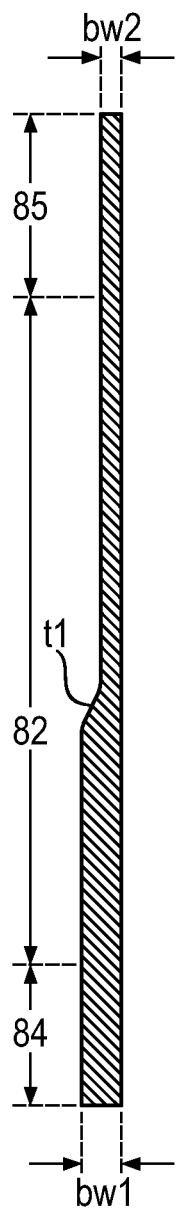
FIGS. 14-15 show two longitudinal cross-sections of the distribution layer of FIG. 13.
Figure 15:
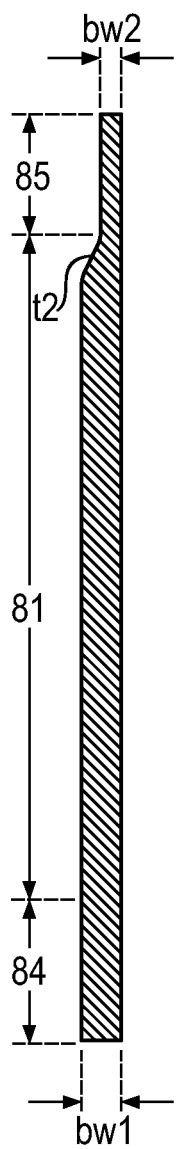
Figure 16:
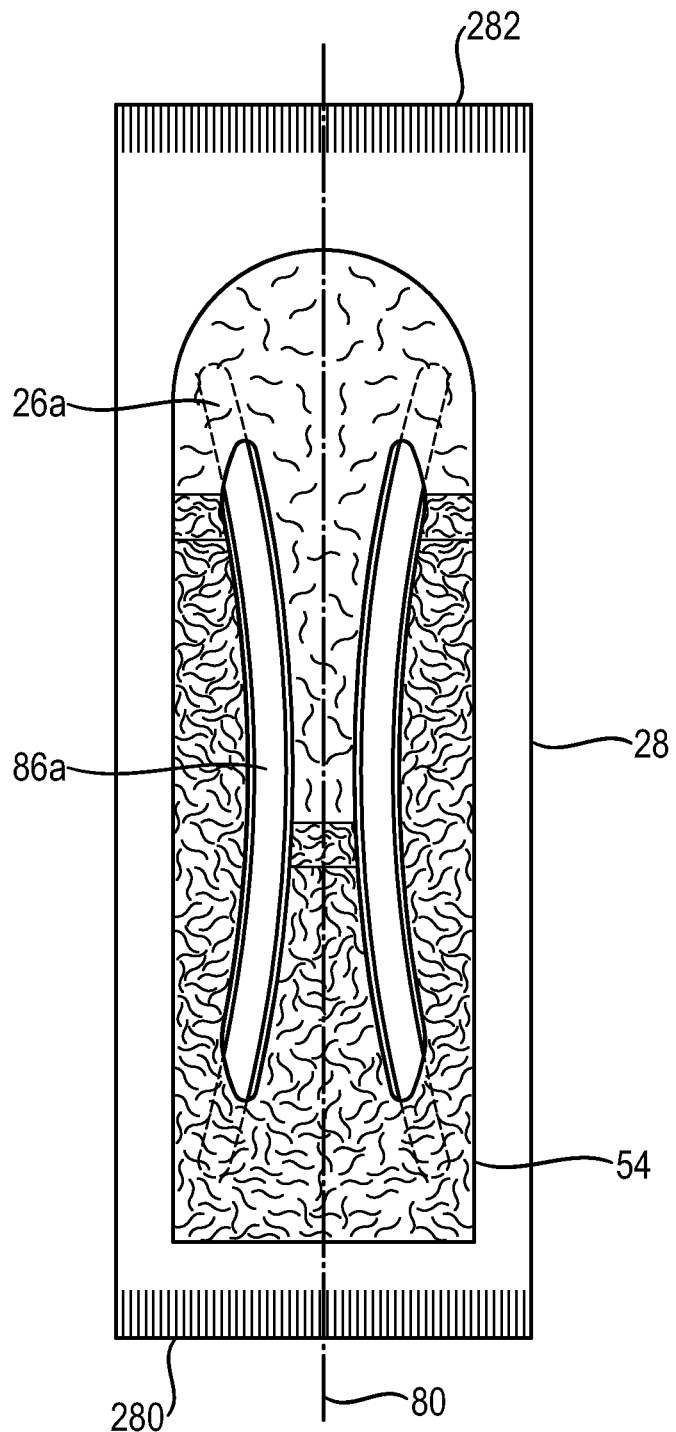
FIG. 16 shows in superposition the distribution layer of FIG. 12 with the absorbent core of FIG. 8.

FIGS. 13-15 show another example of distribution layer, wherein the average basis weight in the lateral areas 81, 83 is higher than the average basis weight in the central area 82, thus having the opposite relationship as for the previous example of FIGS. 4-7. Such a distribution layer may be particularly adapted to an absorbent core with channel-forming areas and having a transversally profiled distribution of absorbent material with a relatively low basis weight in the central absorbent zone compared to the lateral absorbent zones. This type of core may be beneficial if it is desired that the central absorbent zone does not become too stiff in the longitudinal direction when it absorbs fluid and swells. Although the stiffness may thus be reduced in the central zone, the core may remain sufficiently rigid in the lateral areas so that overall the absorbent core refrains from excessive sagging in the crotch region when wet. Excessive sagging may cause the barrier leg cuffs or the gasketing cuffs to lose contact with the skin of the users, thus raising the risk of side leakage outside of the article, and should be avoided. The same general considerations as for the previous example otherwise apply for this example. FIG. 16 shows the superposition of the distribution layer of FIG. 13-15 with an absorbent core comprising channel-forming areas as previously discussed.

FIGS. 17-19 show another example of distribution layer having three regions of different basis weight. In this example, the distribution layer is rectangular (thus not shaped), as seen from above. The region of high basis weight bw1 of the distribution layer is entirely contained in the central area 82 between the channels 86a, 86b. The region of medium basis weight bw2 is present in most of the lateral areas 81, 83 and in the front area 84. The basis weight further diminishes towards the back edge of the distribution layer in the central and lateral areas. The region having the lowest basis weight bw3 comprises the back area 85 of the distribution layer and a small portion of the adjoining central and lateral areas. Gradual transition zones t1, t2, t3 separate the different regions of constant basis weight in the longitudinal direction. The basis weight transition is discrete in the transversal direction between the central area and the lateral areas. Such a distribution layer may be particularly useful for use together with an absorbent core having a rectangular absorbent material deposition area and concentrating the absorbent material in a central zone between its channel-forming areas (if there are present).

FIGS. 20-22 show another example of distribution layer. This distribution layer is shaped (in other words not rectangular), in particular it tapers transversally towards its middle. This distribution layer also comprises four different regions having different basis weight separated by transition zones. The region of highest basis weight bw1 is entirely contained between the channels 86a, 86b in the central area 82. The basis weight gradually tapers towards the front and back end of the central area until it reaches a region of medium basis weight bw2 on each side. The distribution material in the lateral areas 81, 83 also has a medium basis weight bw2 for almost the whole length of the lateral areas. The basis weight further gradually diminishes through a transition zone t2 towards the front edge of the distribution layer to a region of lower basis weight bw3. Similarly, the basis weight of the distribution layer gradually diminishes towards the back edge of the distribution layer through a transition zone t3 until it reaches a region where the basis weight bw4 is lowest. The region of lowest basis weight bw4 is entirely comprised in the back area 85. Different gradual transition zones t1, t2, t3, t4 separate the different regions of constant basis weight in the longitudinal direction. The basis weight transition is discrete in the transversal direction through the channels between the central area and the lateral areas along the majority of the length of the channels. Such a distribution layer may be particularly useful for use together with an absorbent core having a shaped absorbent material deposition area which has a relatively high concentration of the absorbent material in a central zone between its channel-forming areas (if these are present).

Method for Making the Distribution Layer

Figure 23:
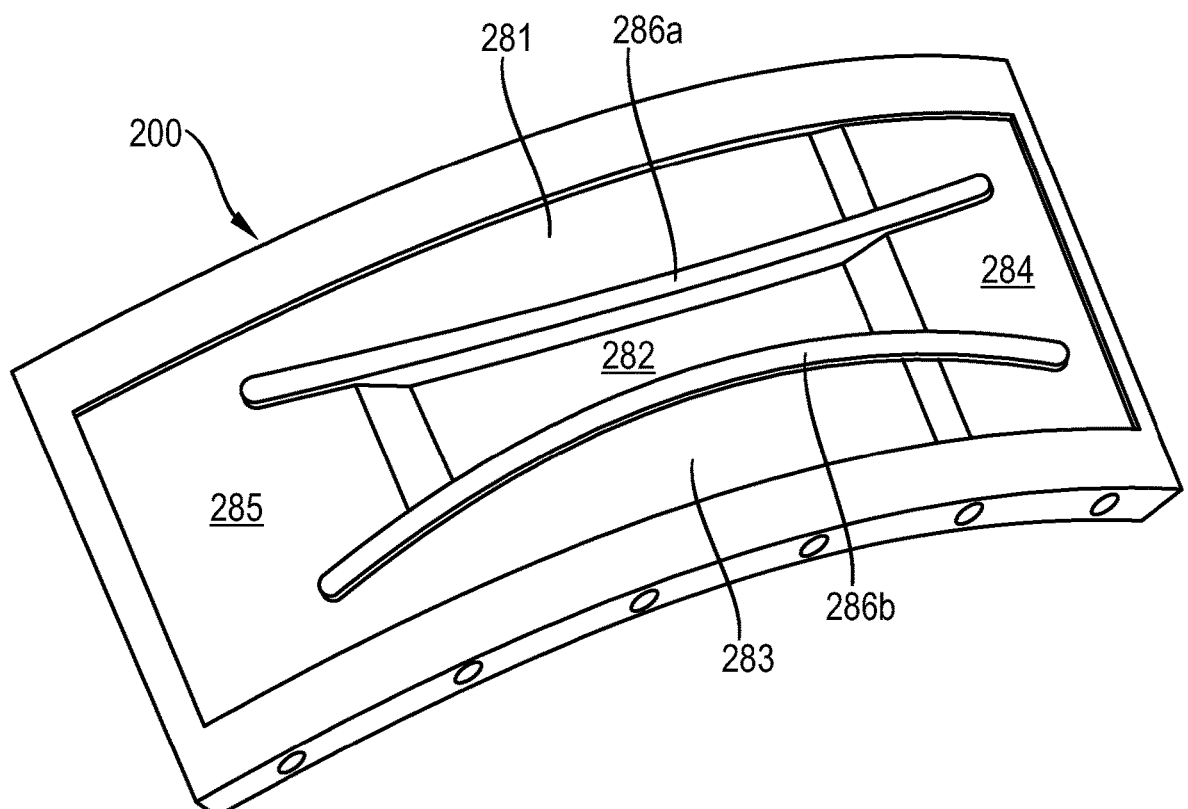
FIG. 23 shows a portion of a laying drum that can be used to form a distribution layer as shown on FIG. 20.

The distribution layer of the invention may be made and integrated in an absorbent article using any typical manufacturing methods known in the art. FIG. 23 shows schematically an individual receptacle or mold 200 that can be used for depositing the fibrous material having a configuration similar to the distribution layer exemplified in FIG. 17. A plurality of such molds may be arranged in a repeating manner along the circumference of a drum in an air-laying chamber, as is known in the art. The bottom of the mold may comprise a grid connected to a source of vacuum so that the fibers are pulled and deposited in the mold. Two elongated protuberances 286a, 286b are flush with the frame of the receptacle, so that substantially no fibers deposit in these areas, thus forming the material-free channels 86a, 86b of the distribution layer. The mold further comprises zones of different depths, for example a zone of lowest depth zone 285 which will form the back area 85 of the distribution layer, a zone of maximum depth 282 corresponding to the central area 82 of the distribution layer, and two lateral zones 281, 283 of medium depth corresponding to the lateral areas 81, 83 of the distribution layer.

Example of Article in a Pant Form

As indicated previously, the invention may be also used in absorbent articles presented in the form of a pant or underwear (herein "pant"). In these articles, the waist and the leg openings are pre-formed during manufacture so that the article can be put on like underwear. These pant articles typically have a front waist panel and a back waist panel which are sealed together via side seams. The side seams can be broken to remove and discard the article and are typically not re-fastenable. The front and back waist panels are typically elasticized. Pants are used as taped diapers on babies and younger children for day wear and for overnight dryness, as training pant for older children at the toilet training stage, and also as adult incontinence protection.

The outline of such a pant article is schematically illustrated in perspective on FIG. 24. The pant comprises a front waist panel 110 and a back waist panel 120 shown in dotted lines. The front and back waist panels are joined together at side seams (not represented) to form the waist opening and the leg openings. The waist panels are typically elasticized, either using a material which is inherently elastic to make them (such as a laminate comprising an elastomeric layer between two nonwoven layers) or by sandwiching a plurality of elastic strands 130 between two nonwovens along the width of the panels, as is known in the art. The pants may further comprise a chassis comprising the remaining components of the article, in particular the topsheet 24, the backsheet 25, the absorbent core 28 and barrier cuffs 30 including upstanding barrier leg cuffs. These components may be generally constructed as in previously disclosed for the taped diaper.

FIG. 25 shows a top view of the wearer-facing side of the pant with the side seams opened and the pant flattened out. For clarity of the view, the barrier cuffs 30, the topsheet 24 and an acquisition layer are not shown in FIG. 25. These and the components represented may be generally as previously discussed. For example, the distribution layer 54 comprises a pair of material-free channel areas 86 which can be superposed with a pair of generally parallel channel-forming areas 26 in the absorbent core. The channels in the distribution layer may be typically shorter or have the same length as the channel-forming areas 26 in the core. Of course, many other constructions for pants are known in the art and possible to use in the present invention.

Having described in details the key features of the invention, the following sections provide more details on some of the typical components found in absorbent articles. The materials described below are of course optional and non-limiting, unless explicitly indicated otherwise.

Core Wrap 16, 16'

The absorbent core comprises a core wrap which encloses the absorbent material. The core wrap can typically comprise a substrate for receiving the absorbent material when the core is made. Various core wrap constructions are possible. The core wrap may in particular comprise as represented in the Figures two separate substrates 16, 16' forming the top side and the bottom side of the core wrap respectively. Having two different substrates for example allows separately depositing about half of the absorbent material on each substrate before combining these to form the core wrap. The two substrates may be attached in a C-wrap configuration with two longitudinal seals 284', 286', and optionally a front seal 280' and aback seal 282' as will be detailed further below. However this core wrap construction is not limiting of the invention, as any conventional core wrap construction may also be used, for example a single substrate on a portion of which the absorbent material is deposited and then the rest of the substrate folded over the deposited absorbent material to form the other side of the core. This single substrate construction can then be sealed longitudinally with a single longitudinal edge seal. The core wrap may also comprise two substrates disposed flat in a face to face relation (sandwich).

The substrates may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US2011/0319848A1 and US2011/0250413A1. Nonwoven materials are typically made of synthetic fibers, such as PE, PET and in particular PP fibers. It is also possible than the core wrap may be at least partially formed from a component of the article having another function than substrate for the absorbent material. For example, it is possible that the backsheet may form the bottom side of the core wrap and/or that a distribution layer or the topsheet may form the top side of the core wrap. However, typically the core wrap is made of one or more substrates whose only function is to receive and enclose the absorbent material, as indicated previously.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

As illustrated in FIG. 9, a first substrate 16 may substantially form the whole of the top surface 288 of the core wrap and a second substrate 16' substantially form the whole of the bottom surface 290 of the core wrap, but it is not excluded that this may be the other way round. By "substantially forming the whole of the surface" it is meant that the outwardly extending flaps of the other substrate that have been folded longitudinally may also form part of the surface considered. The substrates are typically substantially planar in the same plane as the absorbent core, and each comprises an external surface and an internal surface. The internal surface is orientated towards the absorbent material and the external surface is the opposite surface. At least one of the substrate comprises at least one, and advantageously two outwardly extending flaps, which are folded around the front, back or side edges of the absorbent core and then attached to the external surface of the other substrate to form at least one so-called C-wrap seal. As seen in FIG. 9, the first substrate 16 may comprise two side flaps laterally extending along the length of the core and which are folded inwardly over each side edge 284, 286 of the absorbent core. The flaps may be attached to the outer surface of the second substrate 16' for example by using an adhesive seal along each C-wrap seal 284', 286'. One or two continuous or semi-continuous lines of glue may be typically applied along the length of the flaps to bond the inner surface of the flaps to the external surface of the other substrate.

As exemplarily represented in FIG. 10, the core may also comprise so-called sandwich seals 280', 282' where the two substrates are bonded along one edge of the core to each other in face-to-face relationship with the inner surface of each substrate bonded to the inner surface of the other substrate. These sandwich seals can for example be formed using a hotmelt glue applied in a series of stripes in a direction perpendicular of the edge, as shown on the front edge 280 and back edge 282 of the core on FIG. 8 for example.

The substrates may typically be commercially supplied as rolls of material of several hundred meters of length. Each roll is then integrated in the converting line and unrolled at high speed while the auxiliary adhesive, the absorbent material and the fibrous thermoplastic adhesive layer if present are deposited or applied on the substrate and then further converted into an absorbent core when a core wrap enclosing the absorbent material is formed by the second substrate. Typically the machine direction (MD) of the converting line may correspond to the longitudinal direction (y) of the substrate/core and the cross-machine direction (CD) to the transversal direction (x) of the substrate/core. The substrates may be cut along the front and back edges of the core 280, 282 to individualize the core.

Absorbent Material 60

The absorbent material may be any known absorbent material known in the art, but will typically comprise or consist of superabsorbent polymers (herein referred to as "SAP"). The SAP may be typically in particulate forms (superabsorbent polymer particles), optionally mixed with cellulose fibers, but it not excluded that other forms of SAP may be used such as a superabsorbent polymer foam for example. The SAP useful in the present invention includes a variety of water-insoluble, but water-swellable polymers capable of absorbing large quantities of fluids. The term "superabsorbent polymer" refers herein to absorbent materials, which may be cross-linked polymeric materials, that can typically absorb at least 10 times their weight of an aqueous 0.9% saline solution as measured using the Centrifuge Retention Capacity (CRC) test (EDANA method WSP 241.2.R3 (12). The SAP may in particular have a CRC value of more than 20 g/g, or more than 24 g/g, or of from 20 to 50 g/g, or from 20 to 40 g/g, or 24 to 30 g/g.

The absorbent material may comprise a relative high amount of SAP, in particular the absorbent material may comprise at least 80%, in particular at least 85%, 90%, 95% and up to 100% of SAP by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus consist or consist essentially of SAP. The core wrap is not considered as absorbent material for the purpose of calculating the percentage of SAP in the absorbent core. When the absorbent material comprises cellulose fibers, the content of SAP may typically range from 60% to 80% by weight of the absorbent material.

The superabsorbent polymers may be in particulate form so as to be flowable in the dry state and thus easily deposited on a substrate. Typical particulate absorbent polymer materials are made of poly(meth)acrylic acid polymers. However, starch-based particulate absorbent polymer materials may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in WO07/047598, WO07/046052, WO2009/155265 and WO 2009/155264. Suitable superabsorbent polymer particles may be obtained by current state of the art production processes, for example as described in WO2006/083584. The superabsorbent polymers are preferably internally cross-linked, i.e. the polymerization is carried out in the presence of compounds having two or more polymerizable groups which can be free-radically copolymerized into the polymer network. In some embodiments, the SAP are formed from polyacrylic acid polymers/polyacrylate polymers, for example having a neutralization degree of from 60% to 90%, or about 75%, having for example sodium counter ions.

The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP may be in the form of spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 µm to 850 µm, preferably from 100 µm to 710 µm, more preferably from 150 µm to 650 µm, as measured according to EDANA method WSP 220.2-05. SAP having a relatively low particle size help to increase the surface area of the absorbent material which is in contact with liquid exudates and therefore support fast absorption of liquid exudates.

The absorbent core typically comprises only one type of SAP, but it is not excluded that a blend of different SAPs may be used. The fluid permeability of a superabsorbent polymer can be quantified using its Urine Permeability Measurement (UPM) value, as measured in the test disclosed in US patent application number US2014/005622A1. The UPM of the SAP may for example be of at least $10\times10^{-7}$ $cm^3.sec/g$, or at least $30\times10^{-7}$ $cm^3.sec/g$, or at least $50\times10^{-7}$ $cm^3.sec/g$, or more, e.g. at least 80 or $100\times10^{-7}$ $cm^3.sec/g$. The SAP particles may have a time to reach an uptake of 20 g/g (T20) of less than 240s, preferably from 40s to less than 240s, more preferably from 65s to 215s, as measured according to the K(t) test method as described in WO2015/041784 (Peri et al).

Absorbent Material Deposition Area

The absorbent material 60 defines as seen from above as in FIG. 8 an absorbent material deposition area having a periphery that may generally follow the front, back and longitudinal side edges of the core. The absorbent material deposition area can be generally rectangular, for example as shown in FIG. 8, but other shapes can also be used such as a "T" or "Y" or "sand-hour" or "dog-bone" shape. In particular the deposition area may be tapered along its width towards the crotch region of the core. In this way, the absorbent material deposition area may have a relatively narrow width in an area of the core intended to be placed in the crotch region of the absorbent article. This may provide for example better wearing comfort. The absorbent material deposition area may for example have a width (as measured in the transversal direction x) at its narrowest point which is less than about 100 mm, 90 mm, 80 mm, 70 mm, 60 mm or even less than about 50 mm. This narrowest width may be for example at least 5 mm, or at least 10 mm, smaller than the width of the deposition area at its largest point in the front and/or back regions of the deposition area. The channel-forming areas 26 are typically encompassed within the absorbent material area, and are typically completely surrounded by absorbent material, i.e. the channel-forming areas do not extend to any edges of the absorbent material deposition area.

The absorbent material 60 may be deposited on any of the substrates using known techniques, which may allow relatively precise deposition of absorbent material at relatively high speed. In particular the SAP printing technology as disclosed for example in US2006/024433 (Blessing), US2008/0312617 and US2010/0051166A1 (both to Hundorf et al.) may be used. This technique uses a transfer device such as a printing roll to deposit SAP onto a substrate disposed on a grid of a support which may include a plurality of cross-bars 36 extending substantially parallel to each other and spaced apart from one another. The zones 26 substantially free of absorbent material through which the bonding 27 is executed can be formed for example by modifying the pattern of the grid and receiving drums so that no SAP is applied in the selected areas, as exemplary disclosed in US2012/0312491 (Jackels). This technology allows high-speed and precise deposition of SAP on a substrate in particular to provide one or more area(s) substantially free of absorbent material surrounded by absorbent material.

The absorbent material may be substantially continuously distributed in the deposition area. By "substantially continuous" it is meant that at least 50%, or at least to 70% and up to 100% of the deposition area comprises a continuous layer of absorbent material as seen from the top side of the core. The absorbent material may be for example applied as a single continuous layer on one of the substrate, the layer thus directly forming the material deposition area. A continuous layer of absorbent material, in particular of SAP, may also be obtained by combining two absorbent layers having matching (offset) discontinuous absorbent material application pattern wherein the resulting layer is substantially continuously distributed across the absorbent material deposition area, as exemplarily taught in US2008/0312622A1 (Hundorf), and as exemplarily shown on FIGS. 10-11. Each individual absorbent material layer comprises a pattern having absorbent material land areas 75, 75' separated by absorbent material-free junction areas 76, 76'. The absorbent material areas 75 of the first layer correspond substantially to the absorbent material-free junction areas 76' of the second layer and vice versa. As exemplary shown in FIGS. 10-11, the absorbent core 28 may thus comprise a first absorbent layer and a second absorbent layer deposited respectively on the first substrate 16 and second substrate 16' and combined together. The first and second absorbent layers may be deposited as series of transversally oriented dots which immediately after deposition merge into transversal stripes or "land areas" having the desired width. Each absorbent layer may comprise for example between 5 and 50 of these generally transversally orientated land areas. These land areas may have for example a width ranging from 4 to 20 mm, in particular 10 mm, as measured in the longitudinal direction (y). The land areas 75 may be of uniform length in the transversal direction (x) but they may have different width, in particular towards the center or crotch section of the absorbent structure to form so called "dog bone" or "hour-glass" shape, which shows a tapering along its width at least in the crotch zone of the structure. The width of the junction areas 76 between the land areas 75 may typically be shorter than the width of the land areas, for example having a width exemplarily ranging from 0.5 to 6 mm, for example 1 to 2 mm. Of course other patterns of deposition for the absorbent material are possible, for example the absorbent material may be deposited as an array of circular or ovoid land areas, or combination of rectangular land areas with circular or ovoid land areas.

In many applications, the liquid discharge occurs predominantly in one area of the core. For diapers, the liquid may predominantly be released towards the crotch region of the core and to a lesser extent the front of the core. Relatively less liquid may be released towards the back of the core. Thus it may be beneficial to profile the amount of absorbent material along the longitudinal direction of the absorbent structure so that more absorbent material is present in the areas where the liquid is more likely to insult the core.

Channel-Forming Areas 26

The absorbent material deposition area of the core encompasses at least two channel-forming areas 26 which are substantially free of absorbent material and through which core wrap bonds 27 may be formed. By "substantially free" it is meant that zones do not comprise absorbent material except possibly for minimal amount such as involuntary contaminations with absorbent material particles that may occur during the core making process. The top side 288 of the core wrap is attached to the bottom side 290 of the core wrap by core wrap bonds 27 in the channel-forming areas, in particular through these areas substantially free of absorbent material. The channel-forming areas 26 are advantageously surrounded by absorbent material 60. When the absorbent material 60 swells upon absorbing a liquid, the core wrap bonds 27 remain at least initially attached in the channel-forming areas 26. The absorbent material 60 swells in the rest of the core when it absorbs a liquid, so that the core wrap forms one or more visible channels along the channel-forming areas 26 comprising the core wrap bond 27. These channels are three dimensional and can serve to distribute an insulting fluid along their length to a wider area of the core. They may provide a quicker fluid acquisition speed and a better utilization of the absorbent capacity of the core. It is not excluded that the channel-forming areas may be without a core wrap bond, as this may be easier to manufacture, but these non-bonded areas will typically not form permanent three-dimensional channels when wet.

The inner surface of the top side 288 and the inner surface of the bottom side 290 of the core wrap may be bonded together continuously along the channel-forming areas 26, but the core wrap bond 27 may also be discontinuous (intermittent) such as formed by series of point bonds. An auxiliary glue 72 may be used to at least partially form the substrates bond 27. In this case, some pressure may be applied on the substrates in the zones 26 to improve the adhesive bonds between the substrates. If an optional fibrous adhesive 74, 74' is present, it may also help forming the bond 27. If the auxiliary glue is applied as a series of longitudinally orientated continuous slots, the width and frequency of these slots may advantageously be such that at least one slot of auxiliary glue is present at any level of the channel-forming area 26 in the longitudinal direction. For example the slots may be 1 mm wide with a 1 mm distance between each slots, and the channel-forming areas have a width of about 8 mm. Such on average for 4 slots of auxiliary glue will be present in each of the channel-forming area 26. It is of course also possible to form the bonds 27 via other known attachment means, such as pressure bonding, ultrasonic bonding, heat bonding or combination thereof.

The channel-forming areas 26 extend substantially longitudinally, meaning that each zone extends at least as much in the longitudinal direction (y) than in the transversal direction (x), and typically at least twice as much in the longitudinal direction than in the transverse direction (as measured after projection on the respective axis). The channel-forming areas 26 may have a length L' projected on the longitudinal axis 80 of the core that is at least 10% of the length L of the absorbent core, in particular from 20% to 80%. The absorbent material-free channel-forming areas may have a width We along at least part of their length which is at least 2 mm, or at least 3 mm or at least 4 mm, up to for example 20 mm, or 16 mm or 12 mm. The width We of each areas substantially free of absorbent material may be constant through substantially its whole length or may vary along its length.

The channel-forming areas may be typically at least partially curved. In particular the channel-forming areas present in the crotch region may be concave towards the longitudinal axis 80 as illustrated in FIG. 8. Alternatively, it is not excluded that the channel-forming areas may be partially or entirely straight, and in particular longitudinally oriented parallel to the longitudinal axis 80, or curved in the other direction. The channel-forming areas are typically disposed as one or more symmetrical pair(s) relative to the longitudinal axis, and are spaced apart from one another over their whole longitudinal dimension. The shortest spacing distance between the channel-forming areas may be for example at least 5 mm, or at least 10 mm, or at least 16 mm. Furthermore, in order to reduce the risk of fluid leakages, the areas substantially free of absorbent material may advantageously not extend up to any of the edges of the absorbent material deposition area, and are therefore surrounded by and fully encompassed within the absorbent material deposition area of the core. The smallest distance between a channel-forming area and the closest edge of the absorbent material deposition area may be at least 5 mm.

Auxiliary Glue 72

The auxiliary glue 72 is optional. When present, the auxiliary glue may be applied directly over the inner surface of the top side and/or bottom side of the core wrap. The auxiliary glue may at least partially form the bonds 27 between the two sides of the core wrap, through the areas substantially free of absorbent material of the channel-forming areas. The auxiliary glue may also be useful to improve the adhesion between the inner surface of the core wrap and the absorbent material. If a fibrous thermoplastic material 74 is present, such an auxiliary glue may also help adhering the fibrous thermoplastic material to the material-free junction areas 76.

The auxiliary glue may comprise or consist of any kind of thermoplastic hot-melt adhesives used in the field of absorbent core making. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. Exemplary suitable commercial adhesives are available from Fuller under reference number 1358LO and from Henkel under reference numbers DM3800 and DM526. Further information about hotmelt adhesive chemistry is discussed below for the fibrous thermoplastic adhesive layer. The auxiliary glue can be applied by any adhesive applicator known in the field, in particular bead, slot or spray nozzles.

The auxiliary glue 72 was discussed above with reference to the first absorbent substrate 16 which forms the upper side 288 of the absorbent core, and which is placed towards the topsheet 24 in the finished absorbent article 20. This is however not limiting, as the first substrate may alternatively form the bottom side 290 of the absorbent core which is placed towards the backsheet 25 of the article 20. It is also considered that a second auxiliary glue may be applied directly on the second substrate 16' in addition to the first auxiliary glue applied directly on the first substrate 16, in particular in any of the configurations discussed above. This may be particular useful when the absorbent material within the core wrap is formed by two absorbent layers 61, 62 as discussed above.

Microfiber Glue 74, 74'

The absorbent core may comprise a fibrous thermoplastic adhesive material 74 which can be used to further immobilize the absorbent material 60 during the making process of the core and usage of the article. The fibrous thermoplastic adhesive material 74, 74' may be in particular useful to immobilize the layers of absorbent material onto their respective substrate 16, 16' where they have been deposited. These absorbent layers may comprise land areas 75, 75' separated by junction areas 76, 76' as discussed above and the fibrous thermoplastic adhesive material 74 may then be at least partially in contact with the absorbent material in the land areas and at least partially in contact with the substrate layer 16, 16' in the junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material. The fibrous adhesive may be for example sprayed on an absorbent layer after it has been deposited on its substrate during the core making process.

The fibrous thermoplastic adhesive material may have a molecular weight (Mw) of more than 10,000 and a glass transition temperature (Tg) usually below room temperature or $-6°\text{C}<\text{Tg}<16°\text{C}$. Typical concentrations of the polymer in a hotmelt are in the range of about 20% to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%. Exemplary commercial suitable adhesives are NW1151 ex. HB Fuller and H2898 ex. Bostik.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,81,066 (Korpman).

The thermoplastic adhesive material fibers may exemplarily have an average thickness of about 1 to about 50 micrometers or about 1 to about 35 micrometers and an average length of about 5 mm to about 50 mm or about 5 mm to about 30 mm. The auxiliary glue may improve the adhesion of the thermoplastic adhesive material to the substrate. The fibers adhere to each other to form a fibrous layer, which can also be described as a mesh.

Exemplary Method and Apparatus for Making the Absorbent Core

The absorbent cores may be made by any conventional methods known in the art that allow a relative precise and controlled deposition of absorbent material. The articles may be hand-made or industrially produced at high speed on a modern converting line. As mentioned above, the absorbent core of the invention can in particular be made industrially by combining two absorbent structures using the SAP printing method first disclosed in WO2008/155699 (Hundorf et al.) and further developed in WO2012/170798A1 (Jackels et al.), with the adaptations required to obtain the desired distribution of the absorbent material.

Topsheet 24

The topsheet typically forms the majority of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other materials are possible such as porous foams, reticulated foams, woven materials. Typical diaper topsheets have a basis weight of from about 10 gsm to about 28 gsm, in particular between from about 12 gsm to about 18 gsm but higher basis weights are possible if it is desired to provide a very soft feeling wearer-contacting surface for example.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular the topsheet may be a spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T". The topsheet may also have a three-dimensional appearance and feel, or there may be an additional, smaller, three-dimensional layer placed on top of the topsheet. Such three-dimensional additional layers may be for example particularly useful to receive low viscous exudates such as the stool of young babies Examples of such fluid entangled dual layered three-dimensional materials and processes to obtain them have been disclosed for example in US2014/0121623A1, US2014/0121621A1, US2014/0121624A1, US2014/0121625A1.

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet may also include or be treated with antibacterial agents, some examples of which are disclosed in WO95/24173. Further, the topsheet, the backsheet or any portion of the topsheet or backsheet may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 0.012 mm to about 0.051 mm. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film may include at least about 20 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 $g/m^2/24$ hours.

The backsheet may further typically comprise a nonwoven on its most external side to improve softness. Exemplary laminates comprising a breathable film and a nonwoven layer are for example disclosed in WO2014/022,362A1, WO2014/022,652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 $g/m^2/24$ hours. U.S. Pat. No. 5,843,056 for example discloses substantially liquid impermeable, vapor permeable composite backsheet.

Acquisition Layer 52

The absorbent article may comprise an acquisition layer 52, whose function is to quickly acquire the fluid away from the topsheet so as to provide a good dryness for the wearer. The acquisition layer is typically placed directly under the topsheet. The distribution layer may be at least partially disposed under the acquisition layer. The acquisition layer may typically be or comprise a non-woven material, for example a SMS or SMMS material, comprising a spunbonded, a melt-blown and a further spunbonded layer or alternatively a carded chemical-bonded nonwoven. The nonwoven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/148684 (Cramer et al.) and US2005/008839 (Cramer et al.). The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

Another typical acquisition layer, sometimes referred to as secondary topsheet, may for example be a through-air bonded carded web ("TABCW") but many other alternatives material are known in the art and may be used instead. "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). The TABCW material provides a low density, lofty through-air bonded carded web. The web may for example have a specific weight basis level at about 15 gsm to about 120 gsm (gram per m$^2$), in particular about 30 gsm to about 80 gsm. The TABCW material can for example comprise about 3 to about 10 denier staple fibers. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

A further acquisition layer (not shown) may be used in addition to the first acquisition layer described above. For example a tissue layer may be placed between the first acquisition layer and the distribution layer. The tissue may have enhanced capillarity distribution properties compared to the acquisition layers described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and U.S. Pat. No. 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.) The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,86, and 5,591,152.

Front and Back Ears 46, 40

The absorbent article may comprise front ears 46 and back ears 40 as is known in the art in taped diapers. Training pants which are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Absorbent articles such as taped diapers, training pants or adult incontinence pants may typically further comprise cuff components 30 that improve the fit of the article around the legs of the wearer. Such cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 3. Both parts of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the center point C' of the article.

The barrier leg cuffs 34 may be delimited by a proximal edge 36 joined to the rest of the article, typically the topsheet, and a free terminal edge 38 intended to contact and form a seal with the wearer's skin. The barrier leg cuffs 34 may be joined at the proximal edge 36 with the chassis of the article by a bond 37 which may be made for example by adhesive bonding, fusion bonding or combination of known bonding means, for example as disclosed in WO2014/168810A1 (Bianchi et al.). The bond 37 at the proximal edge 36 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings. Typically the barrier leg cuffs 34 are disposed more internally than the gasketing cuffs 32. The barrier leg cuffs are thus also referred to as inner cuffs and the gasketing cuffs as outer cuffs.

For example, U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise at least one elastic waist band (also called elastic waist feature) disposed parallel to and along the back edge of the article and less commonly parallel to and along the front edge of the article. Such waistbands help providing improved fit and containment at the back and/or front edge of the article. The elastic waist feature is generally intended to elastically expand and contract to dynamically fit the wearer's waist. The elastic waist feature may be constructed in a number of different configurations. Non-limiting examples of back and front waistbands can be found in WO2012/177400 and WO2012/177401 (Lawson), and U.S. Pat. Nos. 4,515,595, 4,710,189, 5,221,274 and U.S. Pat. No. 6,336,922 (VanGompel et al.).

Packages

A plurality of articles according to the invention may be packaged in a package for transport and sale. At least 50% of the articles in the package may be according to the invention, and preferably substantially all the articles. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression may be typically sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any of the processes known in the art.

Test Procedures

The values indicated herein are measured according to the methods indicated herein below, unless specified otherwise. All measurements are performed at 21° C.±2° C. and 50%±5% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2.R3 (12).

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10±1 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may be the intersection C' of the longitudinal axis 80' and transversal axis 90' of the absorbent article. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

Water Retention Value Measurement Procedure

The following procedure is utilized to determine the water retention value of fibers using a centrifugal method. A sample of 0.35±0.05 grams of fibers is soaked in a covered container with 100 mL distilled water at 23±2° C. for 17 hours. The soaked fibers are collected on a filter and transferred to a US standard 80-mesh wire basket supported 40 mm above a 60-mesh screened bottom of a centrifuge tube. The tube is covered with a plastic cover and the sample is centrifuged at a relative centrifuge acceleration of 1600±100 gravities (15.7±1.0 km/s$^2$) for 20 minutes. The centrifuged fibers are then removed from the basket and weighed. The weighed fibers are dried to a constant weight at 105° C. in a forced-air oven located in a controlled temperature and humidity environment at 23±2° C. and 50±5% RH. The water retention value (WRV) is calculated as follows:

$$WRV = \frac{(W-D)}{D} \times 100$$

where

W=wet weight of centrifuged fibers

D=dry weight of centrifuged fibers, and

W−D=weight of absorbed water

In-Bag Stack Height Test

The In-Bag stack height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams. Such a testing apparatus is for example illustrated on FIG. 19 of US2008/0312624A1.

Test Procedure: Absorbent article packages are equilibrated at 21±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Determination of the basis weight of the absorbent material in the absorbent core The distribution of the absorbent material in the central and the lateral absorbent zones of the absorbent core is determined by the manufacturer based on the desired product specification. For example, if a SAP printing process is used, the SAP distribution will be determined by the distribution of the cavities on the printing roll and the size of the depressions between the bars. If an air-laid core making process is used, for example to deposit a mix of cellulose fibers and SAP particles as absorbent material, the absorbent material distribution will be determined by the shape of the core mold on which the fibers and SAP particles are deposited. The local basis weight of the absorbent material in the different areas of the absorbent core can be thus directly determined from the manufacturer's specification for the absorbent core's manufacturing tool. For the purpose of calculating the basis weight in the different absorbent zones of the core, any absorbent material-free areas in the plane of the absorbent core such as in the channel-forming areas or any material free recesses at the longitudinal sides of the core (in a profiled core, not represented) are disregarded.

If the manufacturer specifications are not known for a given absorbent core, in particular if the absorbent core was made by a third party, the basis weight of the absorbent material in different sections of the different absorbent zones can be determined in the following manner. The absorbent core is carefully separated from the other components of the article (topsheet, backsheet, . . . ) so as not to damage the absorbent core or modify the distribution of the absorbent material. Then a particular area of interest of the core can be cut out using a die or another suitable means to avoid loss of material, and the area weighted. The absorbent material basis weight in the cut-out area is calculated by dividing the weight of the area (minus the weight of the core wrap) by the size of the area. The basis weight of the core wrap can be determined by taking a sample in an area of the core wrap not comprising the absorbent material and weighing this sample. This procedure can further be repeated on a sufficient amount of similar articles to obtain a good approximation of the basis weight distribution across different sections of the absorbent zones and to smooth out any small variations between individual articles due to process variability.

Misc

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article extending in a longitudinal direction parallel to a longitudinal axis and a transversal direction perpendicular to the longitudinal direction,
   wherein the absorbent article comprises:
   a. a fluid permeable topsheet on the wearer-facing side;
   b. an absorbent core comprising an absorbent material;
   c. a fluid-impermeable backsheet on the garment-facing side; and
   d. a distribution layer between the topsheet and the absorbent core, wherein
   the distribution layer comprises a fibrous material, the distribution layer comprising:
   i. a first and second longitudinally-extending channel substantially free of fibrous material; wherein the first channel is on one side of the longitudinal axis and the second channel is on the other side of the longitudinal axis, wherein the first and second longitudinally-extending channels have a length along the longitudinal axis;
   ii. a central area comprising fibrous material disposed between the first and second longitudinally-extending channels at an average central area basis weight;
   iii. a first and second lateral area comprising fibrous material disposed transversally outwardly of the first channel and the second channel respectively, wherein the first and second lateral areas have an average lateral areas basis weight; and iv. a profiled basis weight configuration spanning the first lateral area, the central area, and the second lateral area profiled in the transversal direction;

wherein the profiled basis weight configuration is present over about 30% to about 100% of the length along the longitudinal axis of the first and second longitudinally-extending channels, wherein the profiled basis weight configuration comprises a first region having-a first basis weight and a second region having a second basis weight, and wherein the first basis weight and the second basis weight differ by at least 20 g/m².

2. The absorbent article according to claim 1, wherein the first basis weight and the second basis weight differ by at least 50 g/m².

3. The absorbent article according to claim 1, wherein the absorbent core comprises a core wrap having a top side and a bottom side, the absorbent material being between the top side and bottom side of the core wrap, and wherein the absorbent core further comprises:
   a. a first and second longitudinally-extending channel-forming area, wherein the first channel-forming area is on one side of the longitudinal axis and the second channel-forming area is on the other side of the longitudinal axis;
   b. a central absorbent zone comprising absorbent material and disposed between the first and the second channel-forming areas; and
   c. a first lateral absorbent zone and a second lateral absorbent zone comprising absorbent material and disposed respectively laterally outwardly of the first channel-forming area and the second channel-forming area.

4. The absorbent article according to claim 3, wherein the channel-forming areas of the absorbent core are substantially free of absorbent material, and the top side of the core wrap is attached to the bottom side of the core wrap through the channel-forming areas.

5. The absorbent article according to claim 3, wherein the first and second channels of the distribution layer are at least partially superposed with the first and second channel-forming areas of the absorbent core.

6. The absorbent article according to claim 1, wherein the fibrous material has a Water Retention Value of from about 2 to about 60, as measured by the Water Retention Value Procedure.

7. The absorbent article according to claim 1, wherein the fibrous material comprises cellulosic fibers.

8. The absorbent article according to claim 1, wherein the distribution layer comprises from about 50% to about 100%, by weight, of cross-linked cellulosic fibers.

9. The absorbent article according to claim 1, wherein the first and second longitudinally-extending channels are curved and wherein the minimum distance between the first and the second longitudinally-extending channels is at least 10 mm.

10. The absorbent article according to claim 1, wherein the absorbent article has a caliper of from about 1.0 mm to about 8.0 mm, as measured according to the Absorbent Article Caliper Test.

11. The absorbent article according to claim 1, wherein the local basis weight of the fibrous material is maximum at a P point, wherein the P point is situated on the longitudinal axis at a distance of 0.30 of the length of the article from the front edge of the article, and the local basis weight is measured on a circular area having a diameter of 10 mm centered on the P point.

12. A package comprising a plurality of absorbent articles according to claim 1.

* * * * *